(12) United States Patent
Wu

(10) Patent No.: US 11,161,849 B2
(45) Date of Patent: Nov. 2, 2021

(54) INHIBITING THE TRANSIENT RECEPTOR POTENTIAL AL ION CHANNEL

(71) Applicant: Eli Lilly and Company, Indianapolis, IN (US)

(72) Inventor: Xinyuan Edward Wu, Chestnut Hill, MA (US)

(73) Assignee: Eli Lilly and Company, Indianapolis, IN (US)

( * ) Notice: Subject to any disclaimer, the term of this patent is extended or adjusted under 35 U.S.C. 154(b) by 15 days.

(21) Appl. No.: 16/763,125

(22) PCT Filed: Jan. 30, 2019

(86) PCT No.: PCT/US2019/015769
§ 371 (c)(1),
(2) Date: May 11, 2020

(87) PCT Pub. No.: WO2019/152465
PCT Pub. Date: Aug. 8, 2019

(65) Prior Publication Data
US 2020/0392136 A1 Dec. 17, 2020

Related U.S. Application Data

(60) Provisional application No. 62/624,276, filed on Jan. 31, 2018.

(51) Int. Cl.
*C07D 473/06* (2006.01)
*A61P 23/00* (2006.01)
*A61K 9/00* (2006.01)

(52) U.S. Cl.
CPC .......... *C07D 473/06* (2013.01); *A61K 9/0053* (2013.01); *A61P 23/00* (2018.01)

(58) Field of Classification Search
CPC ...... C07D 473/06; A61P 23/00; A61K 9/0053
See application file for complete search history.

(56) References Cited

U.S. PATENT DOCUMENTS

| | | | |
|---|---|---|---|
| 8,163,761 | B2 | 4/2012 | Ng et al. |
| 10,221,177 | B2 | 3/2019 | Chenard et al. |
| 10,428,072 | B2 | 10/2019 | Lippa et al. |
| 10,519,158 | B2 | 12/2019 | Chenard et al. |
| 2014/0158116 | A1 | 6/2014 | Chong et al. |
| 2017/0050966 | A1 | 2/2017 | Lippa et al. |
| 2017/0275285 | A1* | 9/2017 | Chenard ............. A61P 11/00 |
| 2018/0230149 | A1 | 8/2018 | Lippa et al. |

FOREIGN PATENT DOCUMENTS

| | | |
|---|---|---|
| WO | 2009/002933 A1 | 12/2008 |
| WO | 2009/140517 A1 | 11/2009 |
| WO | 2010/036821 A1 | 4/2010 |
| WO | 2013/023102 A1 | 2/2013 |
| WO | 2014/026073 A1 | 2/2014 |
| WO | 2014/113671 A1 | 7/2014 |
| WO | 2014/189466 A1 | 11/2014 |
| WO | 2016/044792 A1 | 3/2016 |

* cited by examiner

*Primary Examiner* — Timothy R Rozof
(74) *Attorney, Agent, or Firm* — Nelsen L. Lentz

(57) ABSTRACT

The present invention relates to pharmaceutical compounds of the Formula (I), or a pharmaceutically acceptable salt or composition thereof, and methods of their use for the treatment of pain, respiratory conditions, as well as inhibiting the Transient Receptor Potential A1 ion channel (TRPA1).

14 Claims, No Drawings

INHIBITING THE TRANSIENT RECEPTOR POTENTIAL A1 ION CHANNEL

CROSS-REFERENCE TO RELATED APPLICATIONS

This application claims the benefit of and priority to U.S. Provisional Application No. 62/624,276, filed Jan. 31, 2018, the entire content of which is hereby incorporated by reference herein in its entirety.

TECHNICAL FIELD

The present invention relates to pharmaceutical compounds, compositions, and methods for the treatment of pain, respiratory conditions, as well as inhibiting the Transient Receptor Potential A1 ion channel (TRPA1).

BACKGROUND

Transient Receptor Potential A1 (herein, "TRPA1") is a non-selective cation channel related to pain sensation in humans. TRPA1 is found in sensory neurons and functions as a detector that helps link detection of noxious chemicals, tissue damage, and inflammation to pain. Activation of TRPA1 is believed to cause pain by inducing firing of nociceptive neurons and driving central sensitization in the spinal cord. TRPA1 stimulation can also increase firing of sensory neurons, leading to the release of pro-inflammatory neuropeptides such as NK-A, substance P and CGRP (which induce vasodilation and help recruit immune cells). A variety of endogenous reactive compounds produced during inflammation activate TRPA1 (including 4-hydroxynonenal released during liposome peroxidation; cyclopentane prostaglandins synthesized by COX enzymes; hydrogen peroxide produced by oxidative stress). Activation of TRPA1 also sensitizes TRPA1 to cold. Furthermore, a gain-of-function mutation in TRPA1 causes familial episodic pain syndrome; patients suffering from this condition have episodic pain that may be triggered by cold. Thus, TRPA1 is considered to play a role in pain related to nerve damage, cold allodynia, and inflammatory pain.

Compounds that inhibit the TRPA1 ion channel can be useful, for example, in treating conditions ameliorated, eliminated or prevented by inhibition of the TRPA1 ion channel. For example, pharmaceutical compositions that inhibit TRPA1 can be used to treat pain. Inhibition of TRPA1 (e.g., by genetic ablation and chemical antagonism) has been shown to result in reduced pain behavior in mice and rats. Knockout mice lacking functional TRPA1 have diminished nociceptive responses to TRPA1 activators (including AITC, formalin, acrolein, 4-hydroxynonenal) and, in addition, have greatly reduced thermal and mechanical hypersensitivity in response to the inflammatory mediator bradykinin (e.g., Kwan, K. Y. et al. Neuron 2006, 50, 277-289; Bautista, D. M. et al. Cell 2006, 124, 1269-1282). In animal pain models, down regulation of TRPA1 expression by gene specific antisenses prevented and reversed cold hyperalgesia induced by inflammation and nerve injury (See, e.g., Obata, K. et al., Journal of Clinical Investigation 2005, 115, 2393-2401; Jordt, S. E. et al., Nature 2004, 427, 260-265; Katsura, H. et al., Exploratory Neurology 2006, 200, 112-123). TRPA1 inhibitor compounds are effective in a variety of rodent pain models. TRPA1 inhibitors have been shown to reduce mechanical hypersensitivity and cold allodynia following inflammation induced by Complete Freund's Adjuvant (without altering normal cold sensation in naïve animals) and also to improve function in the rat mono-iodoacetate osteoarthritis model. Materazzi, S et al., European Journal of Physiology 2012, 463(4):561-9; Wei H et al., Anesthesiology 2012, 117(1):137-48; Koivisto, A et al., Pharmacol Res. 2012, 65(1):149-58. TRPA1 inhibitor compounds have demonstrated reduced pain behavior in rodents injected with AITC (mustard oil), formalin, cinnamaldehyde, acrolein, and other TRPA1 activators. TRPA1 inhibitor compounds have also demonstrated efficacy in rodent models for postoperative pain, see, for example, Wei et al., Anesthesiology 2012, 117(1):137-48; chemotherapy induced peripheral neuropathy, see, for example, Trevisan, et al., Cancer Res. 2013 May 15; 73(10):3120-31 Online Mar. 11, 2013; and painful diabetic neuropathy, see, for example, Koivisto et al., Pharmacol Res (2011).

SUMMARY OF THE INVENTION

The present invention provides compounds of Formula I:

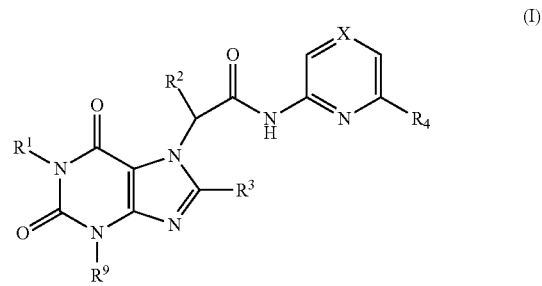

or a pharmaceutically acceptable salt thereof, wherein:

X is N or CH;

$R^1$ is $C_2$-$C_6$ alkyl, $C_2$-$C_6$ alkenyl, $C_2$-$C_6$ alkynyl, —$C_1$-$C_6$ alkyl-O—$C_0$-$C_6$ alkyl, —$C_0$-$C_6$ alkyl-O—$C_1$-$C_6$ alkyl, —$C_1$-$C_6$ alkyl-C(O)—$C_0$-$C_6$ alkyl, —$C_0$-$C_6$ alkyl-C(O)—$C_1$-$C_6$ alkyl, —$C_1$-$C_6$ alkyl-C(O)N($R^7$)$_2$, —$C_1$-$C_6$alkyl-CN, —$C_1$-$C_6$ haloalkyl, aryl, heteroaryl, heterocyclyl, heteroarylalkyl, or heterocyclylalkyl, each of which is substituted with $(R^6)_{1-7}$;

$R^2$ is H or $C_1$-$C_6$ alkyl;

$R^3$ is H or $C_1$-$C_6$ alkyl;

$R^4$ is heteroaryl optionally substituted with $(R^5)_{1-3}$;

$R^5$ is independently H, $C_3$-$C_{10}$ heterocyclyl, $C_1$-$C_3$ alkyl, $C_1$-$C_3$ alkoxy, —$C_1$-$C_6$ alkyl-O—$C_0$-$C_6$ alkyl, —$C_0$-$C_6$ alkyl-O—$C_1$-$C_6$ alkyl, —N($C_1$-$C_3$ alkyl)$_2$, $C_1$-$C_6$ haloalkyl, —$C_1$-$C_3$ alkyl- N($R^7$)$_2$, heterocyclylalkyl, halo, or cyano, each of which is optionally substituted with $(R^6)_{1-3}$;

$R^6$ is independently H, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, aryl, heteroaryl, heterocyclyl, arylalkyl, aryloxy, heteroaryloxy, arylalkoxy, heteroarylalkoxy, heteroarylalkyl, haloalkyl, keto, cyano, or halo, or two $R^6$ together with the atoms to which they are attached may form an optionally substituted 3 to 7-membered ring;

$R^7$ is H, $C_1$-$C_6$ alkyl, or $C_1$-$C_6$ haloalkyl; and $R^9$ is H, $CH_2D$, $CHD_2$, or $CD_3$.

In another aspect, the present invention provides compounds of Formula II:

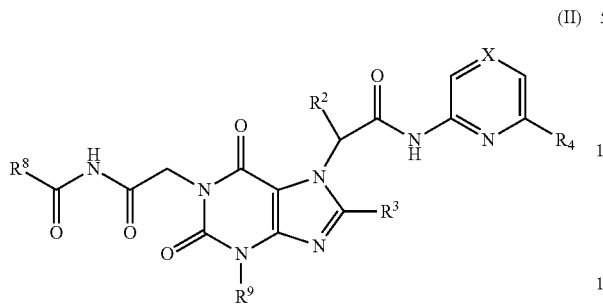

or a pharmaceutically acceptable salt thereof, wherein:
X is N or CH;
$R^2$ is H or $C_1$-$C_6$ alkyl;
$R^3$ is H or $C_1$-$C_6$ alkyl;
$R^4$ is heteroaryl optionally substituted with $(R^5)_{1-3}$;
$R^5$ is independently H, $C_3$-$C_{10}$ heterocyclyl, $C_1$-$C_3$ alkyl, $C_1$-$C_3$ alkoxy, —$C_1$-$C_6$ alkyl-O—$C_0$-$C_6$ alkyl, —$C_0$-$C_6$ alkyl-O—$C_1$-$C_6$ alkyl, —$N(C_1$-$C_3$ alkyl$)_2$, $C_1$-$C_6$ haloalkyl, —$C_1$-$C_3$ alkyl-$N(R^7)_2$, heterocyclylalkyl, halo, or cyano, each of which is optionally substituted with $(R^6)_{1-3}$;
$R^6$ is independently H, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, aryl, heteroaryl, heterocyclyl, arylalkyl, aryloxy, heteroaryloxy, arylalkoxy, heteroarylalkoxy, heteroarylalkyl, haloalkyl, keto, cyano, or halo, or two $R^6$ together with the atoms to which they are attached may form an optionally substituted 3 to 7-membered ring;
$R^7$ is H, $C_1$-$C_6$ alkyl, or $C_1$-$C_6$ haloalkyl;
$R^8$ is H or $C_1$-$C_6$ alkyl; and
$R^9$ is H, $CD_3$, or $C_1$-$C_6$ alkyl.

In another aspect, the present invention provides compounds of Formula III:

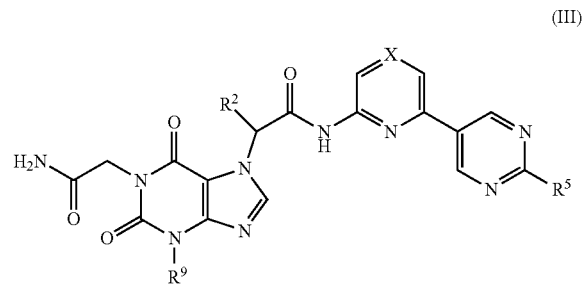

or a pharmaceutically acceptable salt thereof, wherein:
X is N or CH;
$R^2$ is H or $C_1$-$C_6$ alkyl;
$R^5$ is H, $C_3$-$C_{10}$ heterocyclyl, $C_1$-$C_3$ alkyl, $C_1$-$C_3$ alkoxy, —$C_1$-$C_6$ alkyl-O—$C_0$-$C_6$ alkyl, —$C_0$-$C_6$ alkyl-O—$C_1$-$C_6$ alkyl, —$N(C_1$-$C_3$ alkyl$)_2$, $C_1$-$C_6$ haloalkyl, —$C_1$-$C_3$ alkyl-$N(R^7)_2$, heterocyclylalkyl, halo, or cyano, each of which is optionally substituted with $(R^6)_{1-3}$;
$R^6$ is independently H, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, aryl, heteroaryl, heterocyclyl, arylalkyl, aryloxy, heteroaryloxy, arylalkoxy, heteroarylalkoxy, heteroarylalkyl, haloalkyl, keto, cyano, or halo, or two $R^6$ together with the atoms to which they are attached may form an optionally substituted 3 to 7-membered ring; and
$R^7$ is H, $C_1$-$C_6$ alkyl, or $C_1$-$C_6$ haloalkyl; and
$R^9$ is H, $CD_3$, or $C_1$-$C_6$ alkyl.

The present invention further provides compositions comprising a compound of Formula (I) and a pharmaceutically acceptable excipient, diluent or carrier.

The compounds and compositions described herein can be used to treat various disorders in a subject. For example, described herein are methods of treatment such as a method of treating a TRPA1 mediated disorder in a subject, the method comprising administering an effective amount of a compound of Formula (I), (II), or (III), or a pharmaceutically acceptable salt thereof. Methods of treating pain in a subject, the method comprising administering an effective amount of a compound of Formula (I), (II), or (III), or a pharmaceutically acceptable salt thereof are also described herein. Exemplary types of pain include neuropathic pain, e.g., painful diabetic neuropathy, chemotherapy-induced peripheral neuropathy, lower back pain, trigeminal neuralgia, post-herpetic neuralgia, sciatica, and complex regional pain syndrome; inflammatory pain, e.g., from rheumatoid arthritis, osteoarthritis, temperomandibular disorder, PDN or CIPN; visceral pain, e.g., from pancreatitis, inflammatory bowel disease, colitis, Crohn's disease, endometriosis, pelvic pain, and angina; pain selected from the group: cancer pain, burn pain, oral pain, crush and injury-induced pain, incisional pain, bone pain, sickle cell disease pain, fibromyalgia and musculoskeletal pain; or pain from hyperalgesia or allodynia.

DETAILED DESCRIPTION

The present invention provides compounds of Formula I:

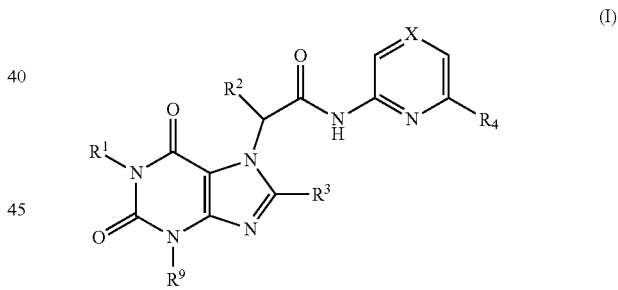

or a pharmaceutically acceptable salt thereof, wherein:
X is N or CH;
$R^1$ is $C_2$-$C_6$ alkyl, $C_2$-$C_6$ alkenyl, $C_2$-$C_6$ alkynyl, —$C_1$-$C_6$ alkyl-O—$C_0$-$C_6$ alkyl, —$C_0$-$C_6$ alkyl-O—$C_1$-$C_6$ alkyl, —$C_1$-$C_6$ alkyl-C(O)—$C_0$-$C_6$ alkyl, —$C_0$-$C_6$ alkyl-C(O)—$C_1$-$C_6$ alkyl, —$C_1$-$C_6$ alkyl-C(O)$N(R^7)_2$, —$C_1$-$C_6$alkyl-CN, —$C_1$-$C_6$ haloalkyl, aryl, heteroaryl, heterocyclyl, heteroarylalkyl, or heterocyclylalkyl, each of which is substituted with $(R^6)_{1-7}$;
$R^2$ is H or $C_1$-$C_6$ alkyl;
$R^3$ is H or $C_1$-$C_6$ alkyl;
$R^4$ is heteroaryl optionally substituted with $(R^5)_{1-3}$;
$R^5$ is independently H, $C_3$-$C_{10}$ heterocyclyl, $C_1$-$C_3$ alkyl, $C_1$-$C_3$ alkoxy, —$C_1$-$C_6$ alkyl-O—$C_0$-$C_6$ alkyl, —$C_0$-$C_6$ alkyl-O—$C_1$-$C_6$ alkyl, —$N(C_1$-$C_3$ alkyl$)_2$, $C_1$-$C_6$ haloalkyl, —$C_1$-$C_3$ alkyl-$N(R^7)_2$, heterocyclylalkyl, halo, or cyano, each of which is optionally substituted with $(R^6)_{1-3}$;

$R^6$ is independently H, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, aryl, heteroaryl, heterocyclyl, arylalkyl, aryloxy, heteroaryloxy, arylalkoxy, heteroarylalkoxy, heteroarylalkyl, haloalkyl, keto, cyano, or halo, or two $R^6$ together with the atoms to which they are attached may form an optionally substituted 3 to 7-membered ring;

$R^7$ is H, $C_1$-$C_6$ alkyl, or $C_1$-$C_6$ haloalkyl; and $R^9$ is H, $CH_2D$, $CHD_2$, or $CD_3$.

In some embodiments, $R^1$ is hydroxypropyl, hydroxylethyl, ketopentyl, hydroxymethyl, pyridinylmethyl, oxazolylmethyl, methylisoxazolylmethyl, oxetanylmethyl, oxadiazolylmethyl, methyloxadiazolylmethyl, methoxyethyl, hydroxymethoxypropyl, methoxyketopropyl, ketomethylbutyl, ketopropyl, ketobutyl, acetamido, cyanomethyl, methylacetamido, trifluoroethyl, trifluoropropyl, or butynyl.

In some embodiments, $R^1$ is

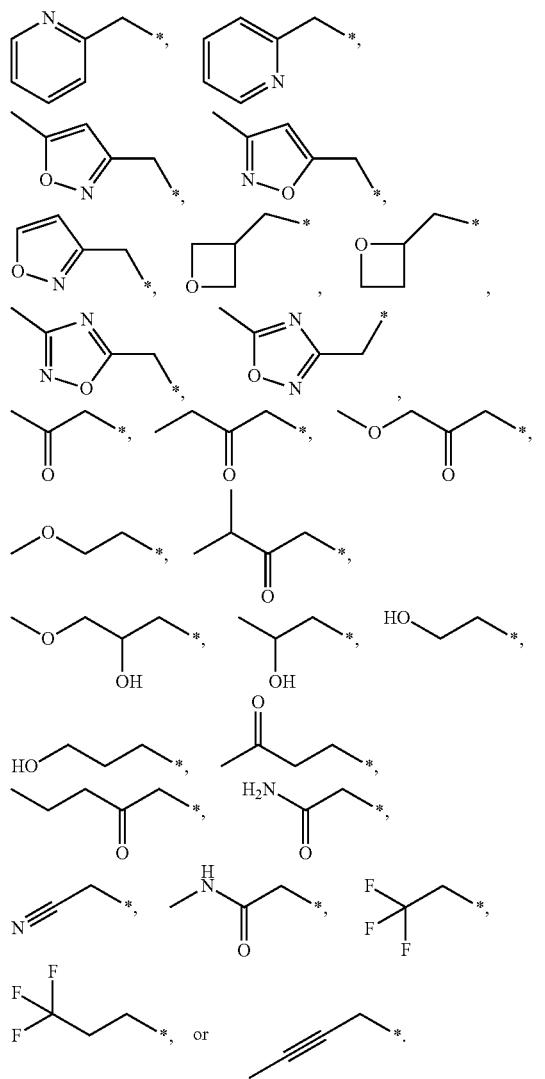

In some embodiments, $R^1$ is heteroarylalkyl optionally substituted with $(R^7)_{1-4}$.

In some embodiments, $R^1$ is 1,2,4 oxadiazolyl methyl optionally substituted with $(R^7)_{1-2}$.

In some embodiments, $R^1$ is

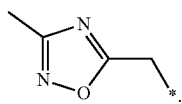

In some embodiments, $R^2$ is methyl.

In some embodiments, $R^2$ is H.

In some embodiments, $R^3$ is H.

In some embodiments, $R^4$ is a 6-membered monocyclic heteroaryl optionally substituted with $(R^5)_{1-3}$.

In some embodiments, $R^4$ is pyridinyl, pyrimidinyl, pyrazinyl, or pyridazinyl, each of which is substituted with $(R^5)_{1-2}$.

In some embodiments, $R^4$ is

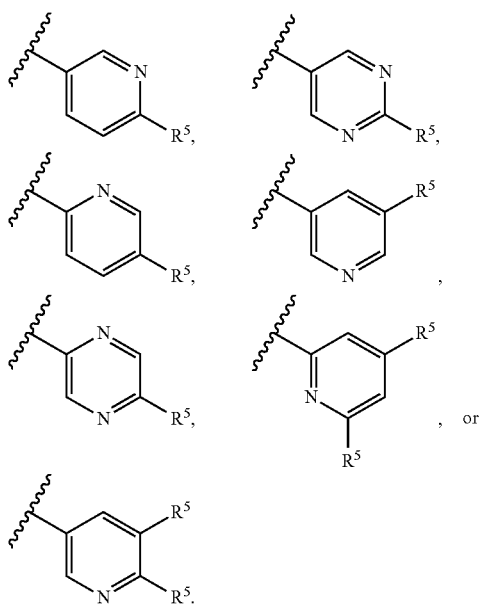

In some embodiments, $R^5$ is independently H, pyrrolidinyl, trifluoromethyl, trifluoroethyl, halo, methyl, isopropyl, cyano, propyl, ethyl, azabicyclohexyl, difluoroazabicyclohexyl, methoxy, methoxyethyl, dialkylamino, or ethoxy, each of which is optionally substituted with $(R^6)_{1-3}$.

In some embodiments, $R^5$ is independently H, —$CF_3$, cyanomethyl, bromine, chlorine, fluorine, methyl, ethyl, isopropyl, cyano,

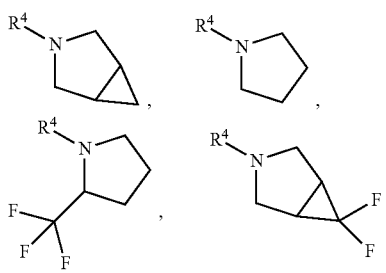

-continued

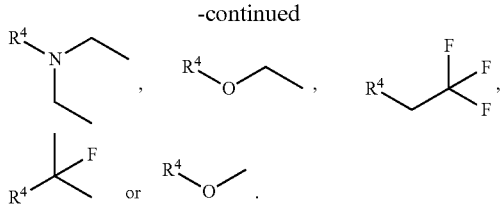

In some embodiments, $R^5$ is $C_1$-$C_3$ alkyl or $C_1$-$C_6$ haloalkyl. In some embodiments, $R^5$ is $CF_3$.

In some embodiments, $R^4$ is

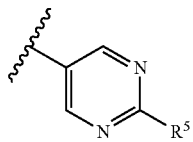

and $R^5$ is $CF_3$.

In some embodiments, $R^7$ is H, methyl, ethyl, or $CF_3$.

In some embodiments, $R^9$ is H. In some embodiments, $R^9$ is $CD_3$.

In some embodiments, $R^1$ is

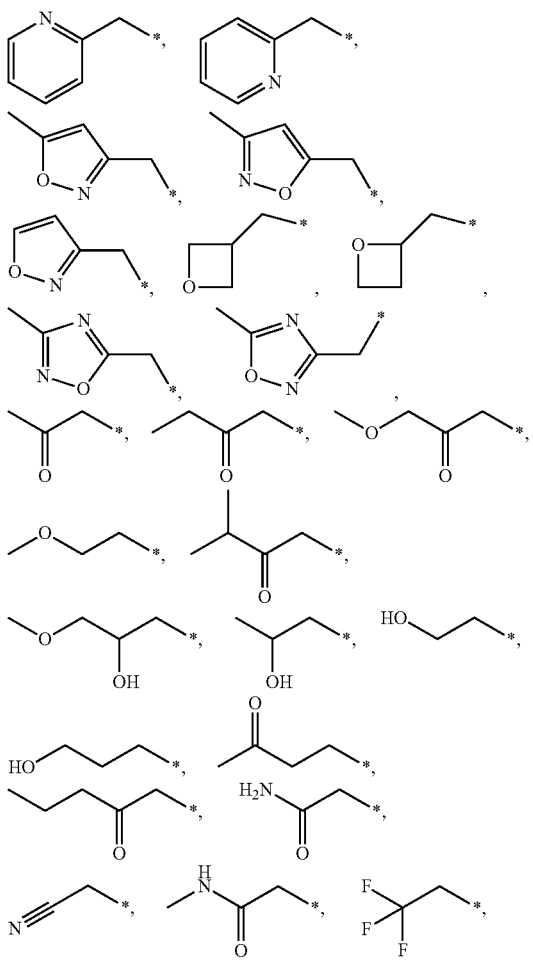

-continued $R^2$ is H or methyl;
$R^4$ is $R^5$ is independently H, —$CF_3$, cyanomethyl, bromine, chlorine, fluorine, methyl, ethyl, isopropyl, cyano, $R^3$ is H or methyl;
$R^7$ is H, methyl, ethyl, or $CF_3$; and
$R^9$ is H or $CD_3$.

In some embodiments, X is N.
In some embodiments, X is CH.
In some embodiments, $R^1$ is —$CH_2$-heteroaryl optionally substituted with $(R^6)_{1-2}$; and
$R^4$ is 6-membered heteroaryl optionally substituted with $(R^5)_{1-3}$.

In some embodiments, $R^1$ is —CH$_2$-heteroaryl optionally substituted with one $R^6$;
$R^2$ is methyl;
$R^3$ is H;
$R^4$ is

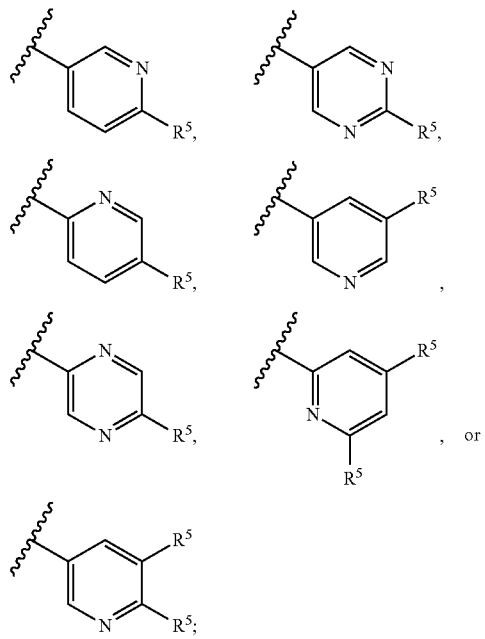

$R^5$ is independently H, —CF$_3$, cyanomethyl, bromine, chlorine, fluorine, methyl, ethyl, isopropyl, cyano,

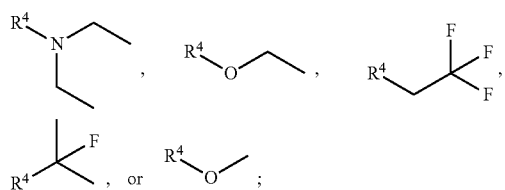

$R^3$ is H or methyl;
$R^7$ is H, methyl, ethyl, or CF$_3$; and
$R^9$ is H or CD$_3$.

In some embodiments, the compound is a compound formula (Ia):

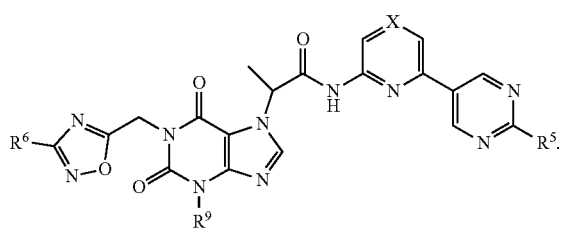

In some embodiments, the compound is a compound of formula (Ib):

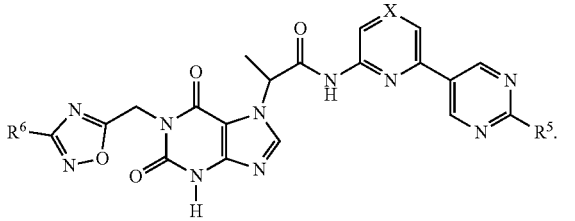

In some embodiments, the compound is a compound of formula (Ic):

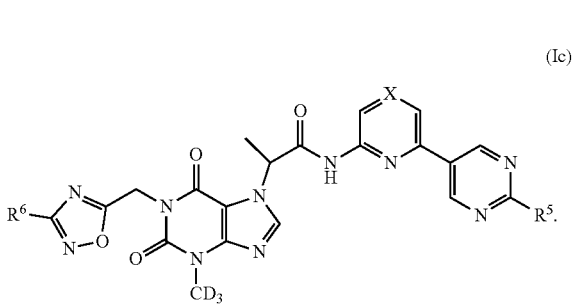

In some embodiments, the compound is selected from the group consisting of:

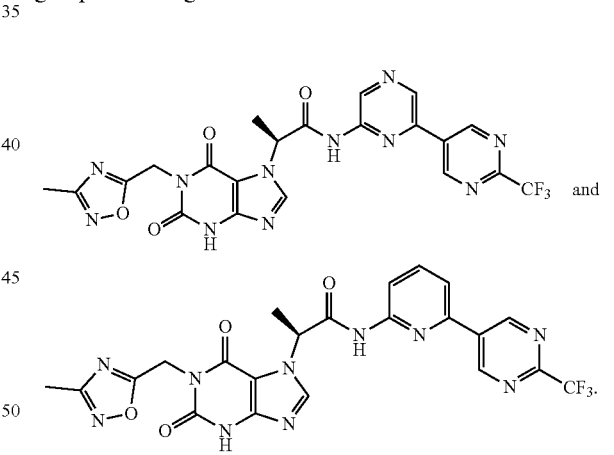

In some embodiments, the compound is selected from the group consisting of:

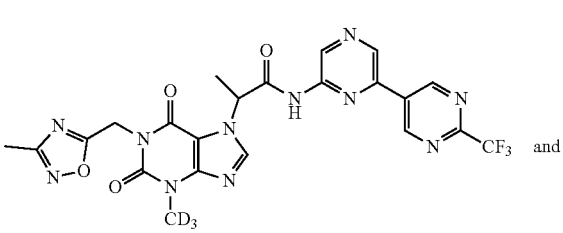

-continued

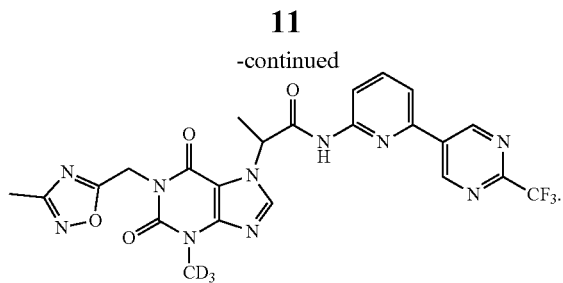

In another aspect, the present invention provides compounds of Formula II:

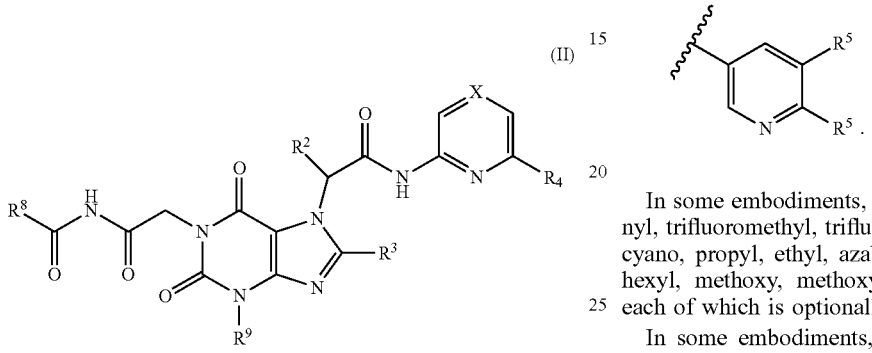

or a pharmaceutically acceptable salt thereof, wherein:
X is N or CH;
$R^2$ is H or $C_1$-$C_6$ alkyl;
$R^3$ is H or $C_1$-$C_6$ alkyl;
$R^4$ is heteroaryl optionally substituted with $(R^5)_{1-3}$;
$R^5$ is independently H, $C_3$-$C_{10}$ heterocyclyl, $C_1$-$C_3$ alkyl, $C_1$-$C_3$ alkoxy, —$C_1$-$C_6$ alkyl-O—$C_0$-$C_6$ alkyl, —$C_0$-$C_6$ alkyl-O—$C_1$-$C_6$ alkyl, —$N(C_1$-$C_3$ alkyl$)_2$, $C_1$-$C_6$ haloalkyl, —$C_1$-$C_3$ alkyl- $N(R^7)_2$, heterocyclylalkyl, halo, or cyano, each of which is optionally substituted with $(R^6)_{1-3}$;
$R^6$ is independently H, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, aryl, heteroaryl, heterocyclyl, arylalkyl, aryloxy, heteroaryloxy, arylalkoxy, heteroarylalkoxy, heteroarylalkyl, haloalkyl, keto, cyano, or halo, or two $R^6$ together with the atoms to which they are attached may form an optionally substituted 3 to 7-membered ring;
$R^7$ is H, $C_1$-$C_6$ alkyl, or $C_1$-$C_6$ haloalkyl;
$R^8$ is H or $C_1$-$C_6$ alkyl; and
$R^9$ is H, $CD_3$, or $C_1$-$C_6$ alkyl.
In some embodiments, $R^9$ is methyl.
In some embodiments, $R^2$ is methyl.
In some embodiments, $R^2$ is H.
In some embodiments, $R^3$ is H.
In some embodiments $R^4$ is a 6-membered monocyclic heteroaryl optionally substituted with $(R^5)_{1-3}$.
In some embodiments $R^4$ is pyridinyl, pyrimidinyl, pyrazinyl, or pyridazinyl, each of which is substituted with $(R^5)_{1-2}$.
In some embodiments, $R^4$ is

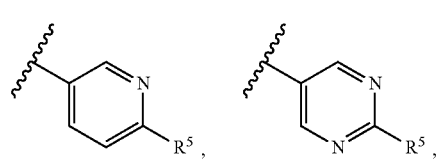

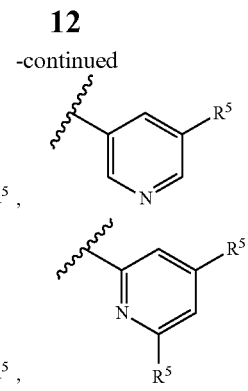

In some embodiments, $R^5$ is independently H, pyrrolidinyl, trifluoromethyl, trifluoroethyl, halo, methyl, isopropyl, cyano, propyl, ethyl, azabicyclohexyl, difluoroazabicyclohexyl, methoxy, methoxyethyl, dialkylamino, or ethoxy, each of which is optionally substituted with $(R^6)_{1-3}$.
In some embodiments, $R^5$ is independently H, —$CF_3$, cyanomethyl, bromine, chlorine, fluorine, methyl, ethyl, isopropyl, cyano,

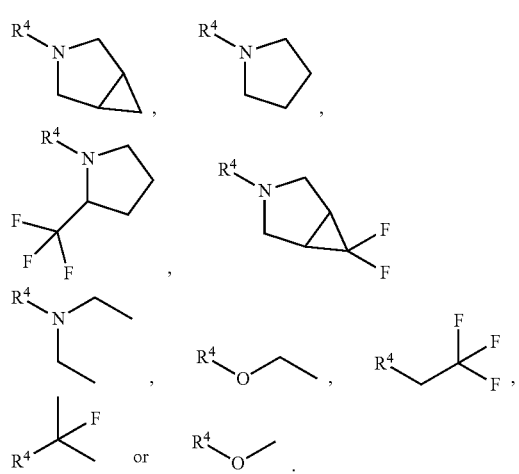

In some embodiments, $R^5$ is $C_1$-$C_3$ alkyl or $C_1$-$C_6$ haloalkyl.
In some embodiments, $R^5$ is $CF_3$.
In some embodiments, $R^4$ is

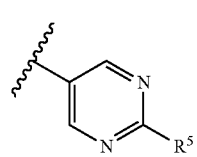

and $R^5$ is $CF_3$.
In some embodiments, $R^7$ is H, methyl, ethyl, or $CF_3$.
In some embodiments, $R^8$ is methyl.
In some embodiments, $R^2$ is H or methyl;
$R^4$ is

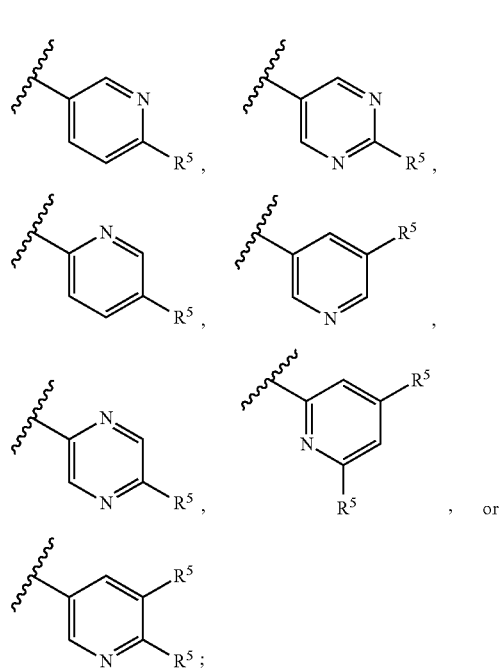

$R^5$ is independently H, —$CF_3$, cyanomethyl, bromine, chlorine, fluorine, methyl, ethyl, isopropyl, cyano,

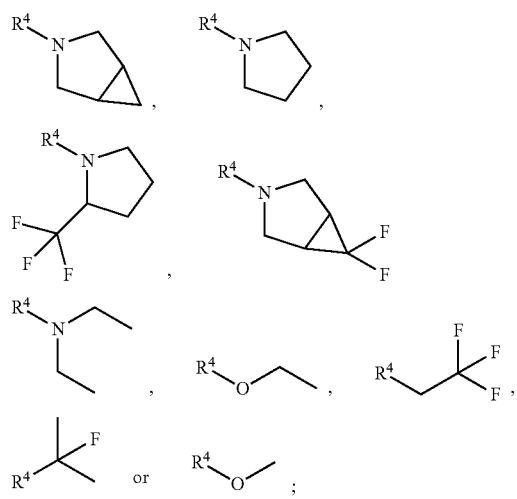

$R^3$ is H or methyl;
$R^7$ is H, methyl, ethyl, or $CF_3$;
$R^8$ is H or $C_1$-$C_6$ alkyl; and
$R^9$ is methyl.

In some embodiments, X is N.
In some embodiments, X is CH.
In some embodiments,
$R^2$ is methyl;
$R^3$ is H;

$R^4$ is

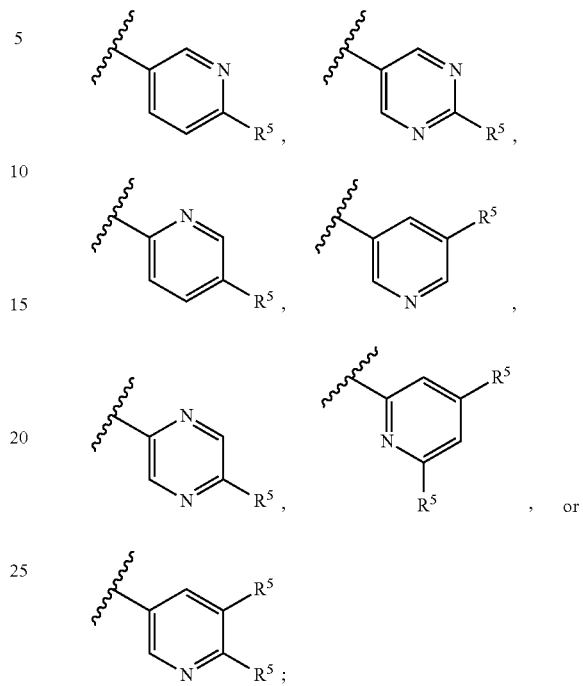

$R^5$ is independently H, —$CF_3$, cyanomethyl, bromine, chlorine, fluorine, methyl, ethyl, isopropyl, cyano, $R^3$ is H or methyl;
$R^7$ is H, methyl, ethyl, or $CF_3$;
$R^8$ is $C_1$-$C_6$ alkyl; and
$R^9$ is methyl.

In some embodiments, the compound is a compound of formula (IIa):

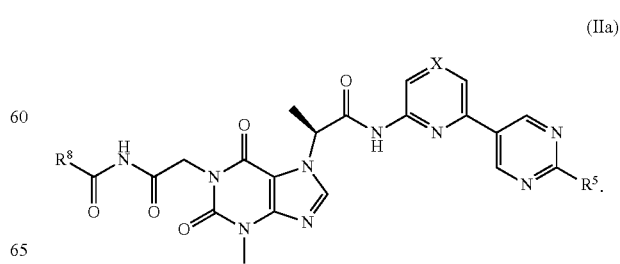

(IIa)

In some embodiments, the compound is selected from the group consisting of:

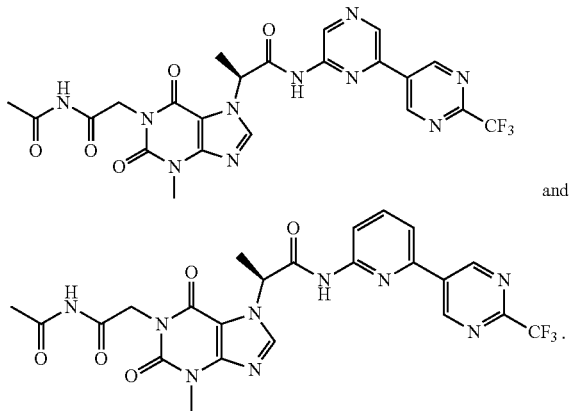

and

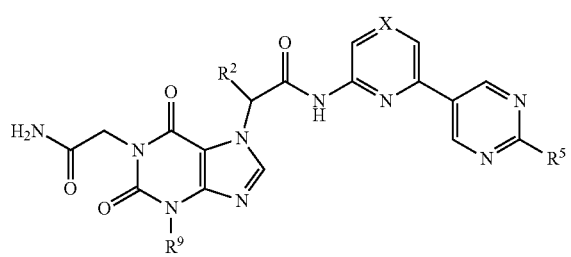

In another aspect, the present invention provides compounds of Formula III:

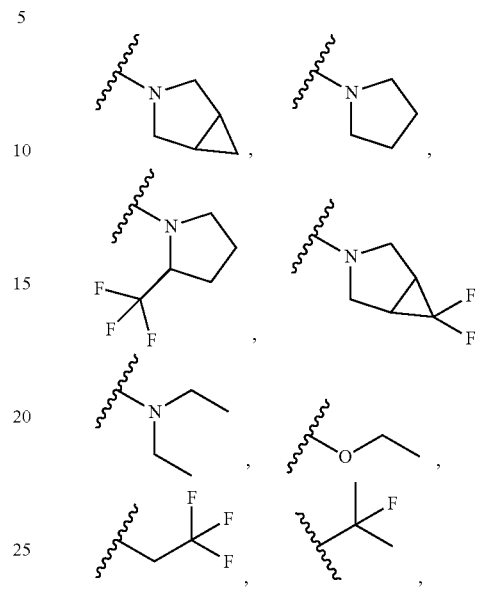

(III)

or a pharmaceutically acceptable salt thereof, wherein:

X is N or CH;

$R^2$ is H or $C_1$-$C_6$ alkyl;

$R^5$ is H, $C_3$-$C_{10}$ heterocyclyl, $C_1$-$C_3$ alkyl, $C_1$-$C_3$ alkoxy, —$C_1$-$C_6$ alkyl-O—$C_0$-$C_6$ alkyl, —$C_0$-$C_6$ alkyl-O—$C_1$-$C_6$ alkyl, —N($C_1$-$C_3$ alkyl)$_2$, $C_1$-$C_6$ haloalkyl, —$C_1$-$C_3$ alkyl-N($R^7$)$_2$, heterocyclylalkyl, halo, or cyano, each of which is optionally substituted with $(R^6)_{1-3}$;

$R^6$ is independently H, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, aryl, heteroaryl, heterocyclyl, arylalkyl, aryloxy, heteroaryloxy, arylalkoxy, heteroarylalkoxy, heteroarylalkyl, haloalkyl, keto, cyano, or halo, or two $R^6$ together with the atoms to which they are attached may form an optionally substituted 3 to 7-membered ring; and $R^7$ is H, $C_1$-$C_6$ alkyl, or $C_1$-$C_6$ haloalkyl; and $R^9$ is H, $CD_3$, or $C_1$-$C_6$ alkyl.

In some embodiments, $R^9$ is methyl.

In some embodiments, $R^2$ is methyl.

In some embodiments, $R^2$ is H.

In some embodiments, $R^5$ is independently H, pyrrolidinyl, trifluoromethyl, trifluoroethyl, halo, methyl, isopropyl, cyano, propyl, ethyl, azabicyclohexyl, difluoroazabicyclohexyl, methoxy, methoxyethyl, dialkylamino, or ethoxy, each of which is optionally substituted with $(R^6)_{1-3}$.

In some embodiments, $R^5$ is independently H, —$CF_3$, cyanomethyl, bromine, chlorine, fluorine, methyl, ethyl, isopropyl, cyano,

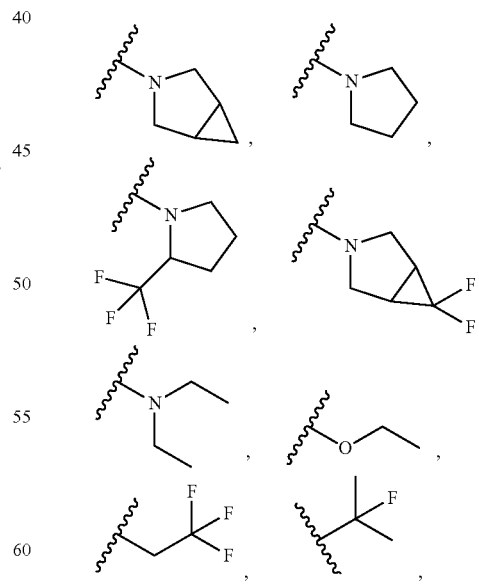

or —$OCH_3$.

In some embodiments, $R^5$ is $C_1$-$C_3$ alkyl or $C_1$-$C_6$ haloalkyl.

In some embodiments, $R^5$ is —$CF_3$.

In some embodiments, $R^7$ is H, methyl, ethyl, or —$CF_3$.

In some embodiments, $R^2$ is H or methyl;

$R^5$ is independently H, —$CF_3$, cyanomethyl, bromine, chlorine, fluorine, methyl, ethyl, isopropyl, cyano, or —$OCH_3$; and $R^9$ is methyl.

In some embodiments, X is N.

In some embodiments, X is CH.

In some embodiments, the compound is a compound of formula (IIIa):

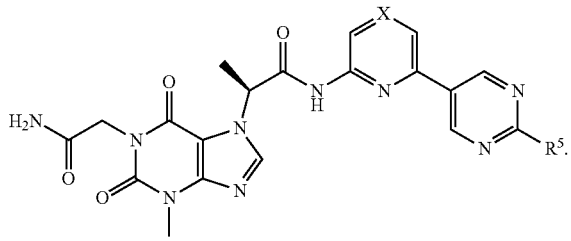

(IIIa)

In some embodiments, the compound is selected from the group consisting of:

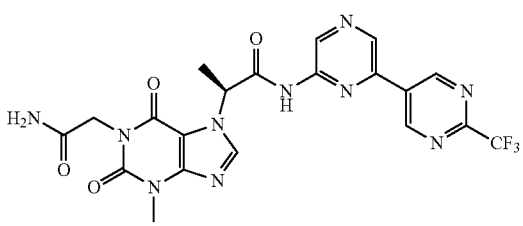

and

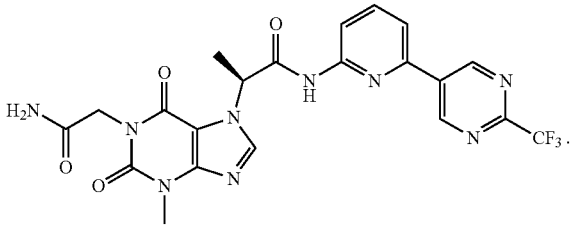

In yet another aspect, the present invention provides a pharmaceutical composition comprising at least one compound of the disclosure or a pharmaceutically acceptable salt thereof in a mixture with a pharmaceutically acceptable excipient, diluent or carrier.

In yet another aspect, the present invention provides a compound of the disclosure for use as a medicament.

In yet another aspect, the present invention provides a compound of the disclosure or a pharmaceutically acceptable salt thereof for use in the treatment of a TRPA1 mediated disorder in a subject.

In some embodiments, the TRPA1 mediated disorder is selected from the group consisting of: pain, inflammatory disease, a dermatological disorder, and a respiratory condition.

In yet another aspect, the present invention provides a compound of the formula:

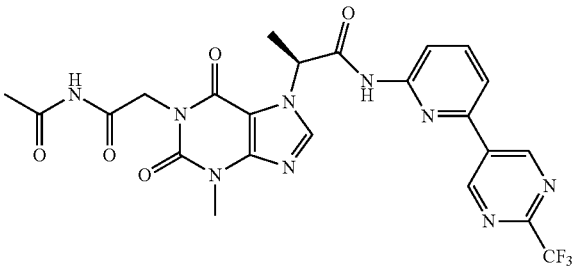 [SMILES: CC(=O)NC(=O)Cn1c(=O)c2c(ncn2[C@@H](C)C(=O)Nc2cccc(-c3cnc(C(F)(F)F)nc3)n2)n(C)c1=O]

wherein the compound is of greater than 95% purity, or a pharmaceutically acceptable salt thereof.

In yet another aspect, the present invention provides a compound of the formula:

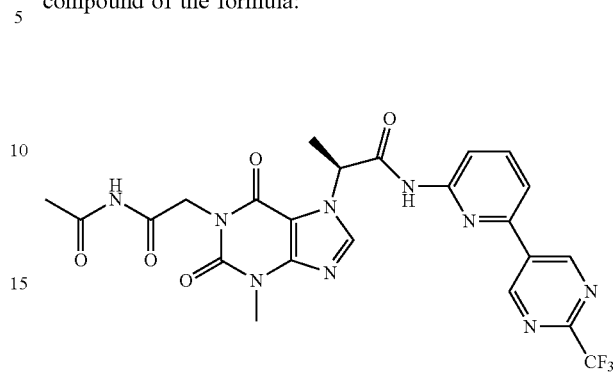

wherein the compound is of greater than 95% purity.

In yet another aspect, the present invention provides a pharmaceutical composition, comprising a compound of the formula:

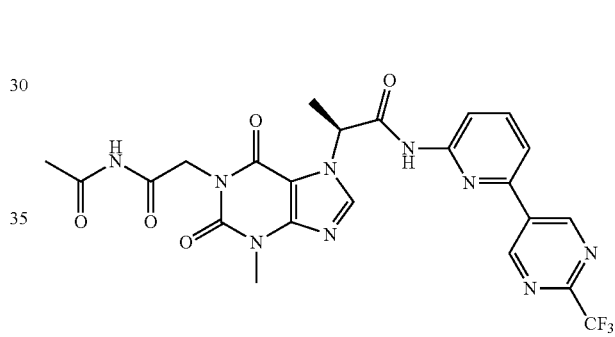

or a pharmaceutically acceptable salt thereof, in a mixture with a pharmaceutically acceptable excipient, diluent, or carrier.

In yet another aspect, the present invention provides a pharmaceutical composition, comprising a compound of the formula:

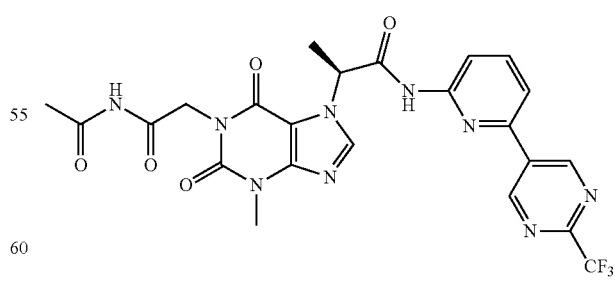

in a mixture with a pharmaceutically acceptable excipient, diluent, or carrier.

In some embodiments, the pharmaceutical composition is for oral administration.

In yet another aspect, the present invention provides a method of treating pain in a subject, comprising administering an effective amount of a compound of the formula:

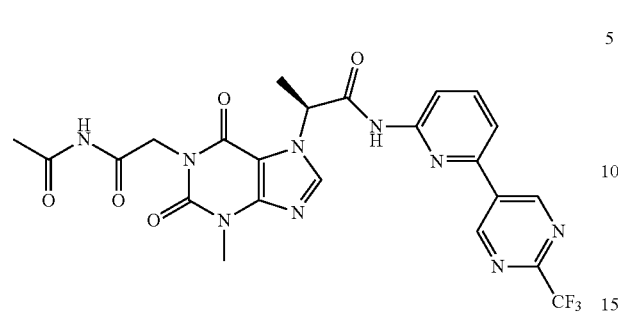

or a pharmaceutically acceptable salt thereof.

In some embodiments, the compound is:

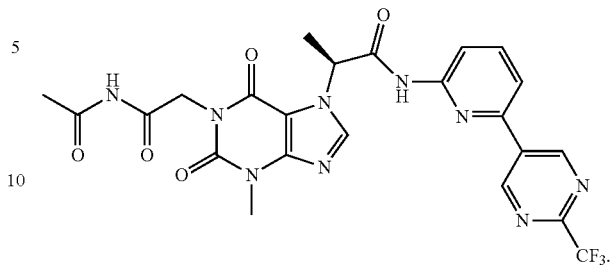

In certain embodiments, exemplary compounds of Formula (I), (II), or (III) include the compounds described in Table 1 and in the Examples.

TABLE 1

| Compound No. | Structure |
|---|---|
| 100 | 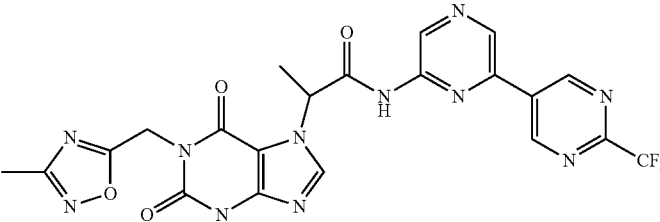 |
| 101 | 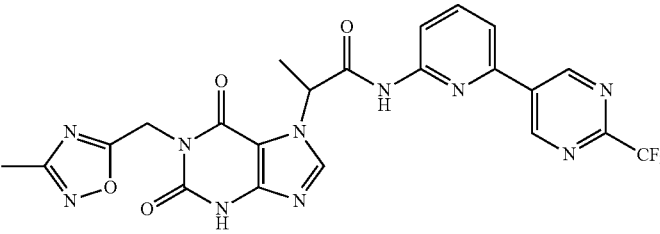 |
| 102 | 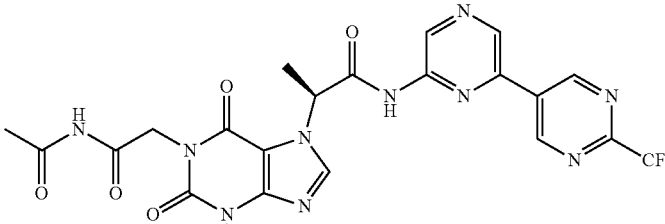 |
| 103 | 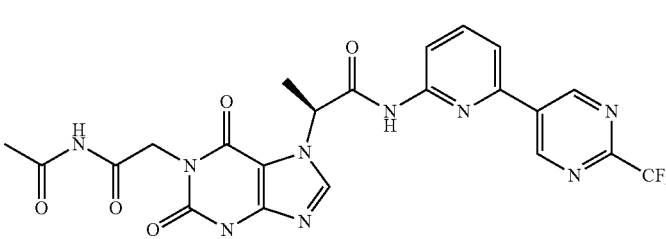 |

TABLE 1-continued

| Compound No. | Structure |
|---|---|
| 104 | 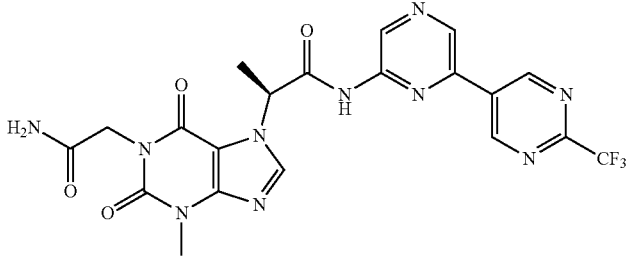 [SMILES: C[C@@H](C(=O)Nc1cncc(-c2cnc(C(F)(F)F)nc2)n1)n1cnc2c1c(=O)n(CC(N)=O)c(=O)n2C] |
| 105 | 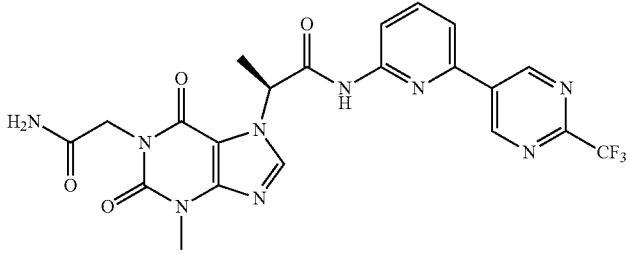 [SMILES: C[C@@H](C(=O)Nc1cccc(-c2cnc(C(F)(F)F)nc2)n1)n1cnc2c1c(=O)n(CC(N)=O)c(=O)n2C] |
| 106 | 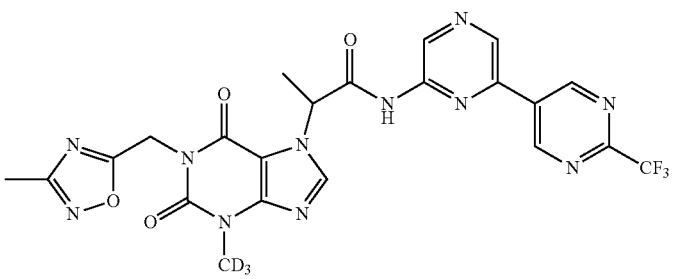 [SMILES: [2H]C([2H])([2H])n1c(=O)n(Cc2nc(C)no2)c(=O)c2c1ncn2C(C)C(=O)Nc1cncc(-c2cnc(C(F)(F)F)nc2)n1] |
| 107 | 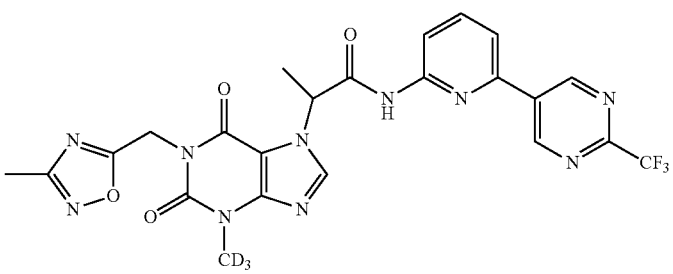 [SMILES: [2H]C([2H])([2H])n1c(=O)n(Cc2nc(C)no2)c(=O)c2c1ncn2C(C)C(=O)Nc1cccc(-c2cnc(C(F)(F)F)nc2)n1] |

This disclosure is not limited in its application to the details of the methods and compositions described herein. Also, the phraseology and terminology used herein is for the purpose of description and should not be regarded as limiting.

Chemical Definitions

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, propyl, butyl, and pentyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

In case a compound of the present invention is depicted in form of a chemical name and as a formula in case of any discrepancy the formula shall prevail.

An asterisk may be used in sub-formulas to indicate the bond which is connected to the core molecule as defined.

As used herein, "alkyl," by itself or as part of another substituent, means, unless otherwise stated, a straight or branched chain, and can have a number of carbon atoms optionally designated (i.e., $C_1$-$C_6$ means one to six carbons).

Examples of saturated hydrocarbon groups include, but are not limited to, groups such as methyl, ethyl, n-propyl, isopropyl, n-butyl, t-butyl, isobutyl, sec-butyl, n-pentyl, isopentyl, homologs and isomers of, for example, n-pentyl, n-hexyl, and the like.

As used herein, "alkenyl" can be a straight or branched hydrocarbon chain, containing at least one double bond, and having from two to six carbon atoms (i.e. $C_2$-$C_6$ alkenyl). Examples of alkenyl groups, include, but are not limited to, groups such as ethenyl (i.e., vinyl), prop-1-enyl (i.e., allyl), but-1-enyl, pent-1-enyl, penta-1,4-dienyl, and the like.

As used herein, "alkoxy" can be a straight chain or branched alkoxy group (e.g. C1-C6 alkyl-O—) having from one to six carbon atoms (i.e., $C_1$-$C_6$ alkoxy). Examples of alkoxy groups, include, but are not limited to, groups such as methoxy, ethoxy, propyloxy, isopropyloxy, butyloxy, isobutyloxy, tert-butyloxy, pentyloxy, or hexyloxy, and the like.

As used herein, "alkynyl" can be a straight or branched hydrocarbon chain, containing at least one triple bond, having from two to six carbon atoms (i.e. $C_2$-$C_6$ alkynyl). Examples of alkynyl groups, include, but are not limited to, groups such as ethynyl, propynyl, butynyl, pentynyl, hexynyl, and the like.

As used herein, "amide" or "amido" refers to a chemical moiety with the formula —C(O)NR$^a$— or —NR$^a$C(O)— wherein R$^a$ is H or $C_1$-$C_6$ alkyl.

As used herein, "amino" or "amine" refers to a —NH$_2$ radical group.

As used herein, "aryl" refers to a polyunsaturated, aromatic, hydrocarbon moiety which can be a single ring or multiple rings (e.g., 1 to 2 rings) which are fused together or linked covalently, having from six to twelve carbon atoms (i.e. $C_6$-$C_{12}$ aryl). Non-limiting examples of aryl groups include phenyl, 1-naphthyl, 2-naphthyl, and 4-biphenyl and the like.

As used herein, "arylalkyl" refers to an (aryl)alkyl-radical wherein aryl and alkyl moieties are as disclosed herein.

As used herein, "aryloxy" refers to —O-(aryl), wherein the aryl moiety is as defined herein.

As used herein, "arylalkoxy" refers to —O-(arylalkyl), wherein the arylalkyl moiety is as defined herein.

As used herein, "cyano" refers to a —CN radical.

As used herein, "cycloalkyl" refers to a monocyclic or polycyclic radical that contains only carbon and hydrogen, and may be saturated, or partially unsaturated. Cycloalkyl groups include groups having from 3 to 10 ring atoms (i.e. $C_3$-$C_{10}$ cycloalkyl). Examples of cycloalkyl groups include, but are not limited to, groups such as cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

As used herein, "halo" or "halogen," independently or as part of another substituent, mean, unless otherwise stated, a fluorine, chlorine, bromine, or iodine atom. The term "halide" by itself or as part of another substituent, refers to a fluoride, chloride, bromide, or iodide atom.

As used herein, "haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine (e.g., —$C_1$-$C_6$ alkyl-$CF_3$, —O—$C_1$-$C_6$ alkyl-$CHF_2$). Non-limiting examples of haloalkyl include trifluoroethyl, trifluoropropyl, trifluoromethyl, fluoromethyl, difluoromethyl, and fluoroisopropyl.

As used herein, "heteroaryl" refers to a 5- to 14-membered aromatic radical (e.g., $C_2$-$C_{13}$ heteroaryl) that includes one or more ring heteroatoms selected from nitrogen, oxygen and sulfur, and which may be a monocyclic or bicyclic ring system. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s) The term "heteroaryl" is intended to include all the possible isomeric forms. Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like.

As used herein, "heterocyclyl" can be a stable 3- to 18-membered non-aromatic mono, di, or tricyclic ring radical that comprises two to twelve carbon atoms and from one to six heteroatoms selected from nitrogen, oxygen and sulfur. Examples of heterocycloalkyl groups include, but are not limited to, groups such as dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, azetidinyl, azabicyclohexyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, and the like.

As used herein, "heteroarylalkyl" refers to refers to an (heteroaryl)alkyl—radical wherein the heteroaryl and alkyl moieties are as disclosed herein.

As used herein, "heteroaryloxy" refers to —O-(heteroaryl), wherein the heteroaryl moiety is as defined herein.

As used herein, "heterocycloalkyl" refers to an (heterocyclyl)alkyl-moiety and can be a stable 3- to 18-membered non-aromatic ring moiety that comprises two to twelve carbon atoms and from one to six heteroatoms selected from nitrogen, oxygen and sulfur. Examples of heterocycloalkyl groups include, but are not limited to, groups such as dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, and the like covalently bonded to one or more alkyl moieties as defined herein.

As used herein, "hydroxy" or "hydroxyl" refers to —OH.

As used herein, "nitro" refers to —$NO_2$.

As used herein, "keto" refers to —C=O.

Many of the terms given above may be used repeatedly in the definition of a formula or group and in each case have one of the meanings given above, independently of one another.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds (e.g., alkyl, alkenyl, alkynyl, cycloalkyl, heterocycloalkyl, aryl, or heteroaryl, any of which may itself be further substituted), as well as halogen, carbonyl (e.g., aldehyde, ketone, ester, carboxyl, or formyl), thiocarbonyl (e.g., thioester, thiocarboxylate, or thioformate), amino, —N($R^b$)($R^c$), wherein each $R^b$ and $R^c$ is independently H or $C_1$-$C_6$ alkyl, cyano, nitro, —$SO_2$N($R^b$)($R^c$), —$SOR^d$, and $S(O)_2R^d$, wherein each $R^b$, $R^c$, and $R^d$ is independently H or $C_1$-$C_6$ alkyl. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Contemplated equivalents of the compounds described above include compounds which otherwise correspond thereto, and which have the same general properties thereof (e.g., the ability to inhibit TRPA1 activity), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Definitions

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, an amount of a compound or combination effective to treat a disorder (e.g., a disorder as described herein), "therapeutically effective amount", "effective amount" or "effective course" refers to an amount of the compound or combination which is effective, upon single or multiple dose administration(s) to a subject, in treating a subject, or in curing, alleviating, relieving or improving a subject with a disorder (e.g., a disorder as described herein) beyond that expected in the absence of such treatment.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds disclosed herein. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19.)

In other cases, the compounds disclosed herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds disclosed herein. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term, "treat" or "treatment," as used herein, refers to the application or administration of a compound, alone or in combination with, an additional agent to a subject, e.g., a subject who has a disorder (e.g., a disorder as described herein), a symptom of a disorder, or a predisposition toward a disorder, with the purpose to cure, heal, alleviate, relieve, alter, remedy, ameliorate, improve or affect the disorder.

As used herein, the term "subject" is intended to include human and non-human animals. Exemplary human subjects include a human subject having a disorder, e.g., a disorder described herein. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The terms "antagonist" and "inhibitor" are used interchangeably to refer to an agent that decreases or suppresses a biological activity, such as to repress an activity of an ion channel, such as TRPA1. TRPA1 inhibitors include inhibitors having any combination of the structural and/or functional properties disclosed herein.

An "effective amount" of, e.g., a TRPA1 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPA1 antagonist for use in the methods of the present invention, includes an amount of a TRPA1 antagonist effective to decrease one or more in vitro or in vivo functions of a TRPA1 channel. Exemplary functions include, but are not limited to, membrane polarization (e.g., an antagonist may prevent depolarization of a cell), ion flux, ion concentration in a cell, outward current, and inward current. Compounds that antagonize TRPA1 function include compounds that antagonize an in vitro or in vivo functional activity of TRPA1. When a particular functional activity is only readily observable in an in vitro assay, the ability of a compound to inhibit TRPA1 function in that in vitro assay serves as a reasonable proxy for the activity of that compound. In certain embodiments, an effective amount is an amount sufficient to inhibit a TRPA1-mediated current and/or the amount sufficient to inhibit TRPA1 mediated ion flux.

The term "hydrate" as used herein, refers to a compound formed by the union of water with the parent compound.

The term "preventing," when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "solvate" as used herein, refers to a compound formed by solvation (e.g., a compound formed by the combination of solvent molecules with molecules or ions of the solute).

The terms "TRPA1", "TRPA1 protein", and "TRPA1 channel" are used interchangeably throughout the application. These terms refer to an ion channel (e.g., a polypeptide) comprising the amino acid sequence set forth in SEQ ID NO: 1, SEQ ID NO:3, or SEQ ID NO: 5 of WO 2007/073505, or an equivalent polypeptide, or a functional bioactive fragment thereof. In certain embodiments, the term refers to a polypeptide comprising, consisting of, or consisting essentially of, the amino acid sequence set forth in SEQ ID NO: 1, SEQ ID NO:3, or SEQ ID NO: 5. TRPA1 includes polypeptides that retain a function of TRPA1 and comprise (i) all or a portion of the amino acid sequence set forth in SEQ ID NO: 1, SEQ ID NO:3 or SEQ ID NO: 5; (ii) the amino acid sequence set forth in SEQ ID NO: 1, SEQ ID NO:3 or SEQ ID NO: 5 with 1 to about 2, 3, 5, 7, 10, 15, 20, 30, 50, 75 or more conservative amino acid substitutions; (iii) an amino acid sequence that is at least 70%, 75%, 80%, 90%, 95%, 96%, 97%, 98%, or 99% identical to SEQ ID NO: 1, SEQ ID NO:3 or SEQ ID NO: 5; and (iv) functional fragments thereof. Polypeptides of the invention also include homologs, e.g., orthologs and paralogs, of SEQ ID NO: 1, SEQ ID NO: 3 or SEQ ID NO: 5.

In some embodiments the methods include treating inflammatory disease in a subject, the method comprising administering an effective amount of a compound of Formula (I), (II), or (III), or a pharmaceutically acceptable salt thereof.

In some embodiments the methods include treating neuropathy in a subject, the method comprising administering an effective amount of a compound of Formula (I), (II), or (III), or a pharmaceutically acceptable salt thereof. In some embodiments, the neuropathy is from diabetes, chemical injury, chemotherapy, and or trauma.

In some embodiments the methods include treating a dermatogological disorder in a subject, the method comprising administering an effective amount of a compound of Formula (I), (II), or (III), or a pharmaceutically acceptable salt thereof. Exemplary dermatogological disorders include atopic dermatitis, acute pruritus, psoriasis, hives, eczema, dyshidrotic eczema, mouth ulcers, and diaper rash.

In some embodiments the methods include treating a respiratory condition in a subject, the method comprising administering an effective amount of a compound of Formula (I), (II), or (III), or a pharmaceutically acceptable salt thereof. Exemplary respiratory conditions include obstructive diseases such as chronic obstructive pulmonary disease. Additional exemplary respiratory conditions include asthma and cough.

Another aspect of the invention features a pharmaceutical preparation suitable for use in a human patient, or for veterinary use, comprising an effective amount of a compound of Formula (I), (II), or (III) (or a salt thereof, or a solvate, hydrate, oxidative metabolite or prodrug of the compound or its salt), and one or more pharmaceutically acceptable excipients. The invention further contemplates the use of compounds of Formula (I), (II), or (III) in the manufacture of a medicament or pharmaceutical preparation to treat or reduce the symptoms of any of the diseases or conditions provided in the specification. The compounds of Formula (I), (II), or (III) for use in treating a particular disease or condition can be formulated for administration via a route appropriate for the particular disease or condition.

Compounds of Formula (I), (II), or (III) can be administered alone or in combination with another therapeutic agent. For instance, the compounds of Formula (I), (II), or (III) can be administered conjointly with one or more of an anti-inflammatory agent, anti-acne agent, anti-wrinkle agent, anti-scarring agent, anti-psoriatic agent, anti-proliferative agent, anti-fungal agent, anti-viral agent, anti-septic agent, anti-migraine agent, keratolytic agent, or a hair growth inhibitor.

Compounds of Formula (I), (II), or (III) can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally, sublingually, or by inhalation. In some embodiments, compounds of Formula (I), (II), or (III) can be administered topically. In some embodiments, compounds of Formula (I), (II), or (III) can be administered orally.

In some embodiments, compounds of Formula (I), (II), or (III) can be administered parentally.

Compounds of Formula (I), (II), or (III) include molecules having an aqueous solubility suitable for oral or parenteral (e.g., intravenous) administration leading to or resulting in the treatment of a disorder described herein, for example the treatment of pain. In some embodiments, the compound is formulated into a composition suitable for oral administration. The potency in inhibiting the TRPA1 ion channel of compounds of Formula (I), (II), or (III) described herein was measured using the method of Example 1. Table 2 discloses the TRPA1 inhibition in vitro potency of exemplary compounds (measured by the method of Example 1).

Preferred compounds of Formula (I), (II), or (III) include compounds that inhibit the TRPA1 ion channel with a $IC_{50}$ value obtained by the method of Example 1 of less than about 1 µM.

Compounds of Formula (I) can inhibit the TRPA1 ion channel. In some embodiments, a compound of Formula (I), (II), or (III) can be administered as part of an oral or parenteral (e.g., intravenous) pharmaceutical composition to treat a disorder described herein (e.g., pain) in a therapeutically effective manner.

Certain compounds disclosed herein may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. For example, if one chiral center is present in a molecule, the invention includes racemic mixtures, enantiomerically enriched mixtures, and substantially enantiomerically or diastereomerically pure compounds. The composition can contain, e.g., more than 50%, more than 60%, more than 70%, more than 80%, more than 90%, more than 95%, or more than 99% of a single enantiomer or diastereomer. Additional asymmetric carbon atoms may be present in a substituent such as an alkyl group. All such isomers, as well as mixtures thereof, are intended to be included in this invention.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

ee=(90−10)/100=80%.

Thus, a composition containing 90% of one enantiomer and 10% of the other enantiomer is said to have an enantiomeric excess of 80%.

The "diastereomeric excess" or "% diastereomeric excess" of a composition can be calculated using the equation shown below. In the example shown below a composition contains 90% of one diastereomer, and 10% of another enantiomer.

ee=(90−10)/100=80%.

Thus, a composition containing 90% of one diastereomer and 10% of the other diastereomer is said to have an diastereomeric excess of 80%.

In addition, compounds of Formula (I), (II), or (III) can include one or more isotopes of the atoms present in Formula (I), (II), or (III). For example, compounds of Formula (I), (II), or (III) can include: those in which H (or hydrogen) is replaced with any isotopic form of hydrogen including $^1H$, $^2H$ or D (Deuterium), and $^3H$ (Tritium); those in which C is replaced with any isotopic form of carbon including $^{12}C$, $^{13}C$, and $^{14}C$; those in which O is replaced with any isotopic form of oxygen including $^{16}O$, $^{17}O$ and $^{18}O$; those in which N is replaced with any isotopic form of nitrogen including $^{13}N$, $^{14}N$ and $^{15}N$; those in which P is replaced with any isotopic form of phosphorous including $^{31}P$ and $^{32}P$; those in which S is replaced with any isotopic form of sulfur including $^{32}S$ and $^{35}S$; those in which F is replaced with any isotopic form of fluorine including $^{19}F$ and $^{18}F$; and the like. In an embodiment, compounds represented by Formula (I), (II), or (III) comprise isomers of the atoms therein in their naturally occurring abundance.

In some embodiments, compounds described herein (e.g., a compound of Formula (I), (II), or (III)), are deuterium-enriched.

Deuterium (D or $^2H$) is a stable, non-radioactive isotope of hydrogen and has an atomic weight of 2.0144. Hydrogen naturally occurs as a mixture of the isotopes $^1H$ (hydrogen or protium), D ($^2H$ or deuterium), and T ($^3H$ or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015% should be considered unnatural and, as a result, novel over their non-enriched counterparts. The effects of deuterium modification on a compound's metabolic properties are not predictable, even when deuterium atoms are incorporated at known sites of metabolism. Only by actually preparing and testing a deuterated compound can one determine if and how the rate of metabolism will differ from that of its non-deuterated counterpart. See, for example, Fukuto et al. (J. Med. Chem. 1991, 34, 2871-76). Many compounds have multiple sites where metabolism is possible. The site(s) where deuterium substitution is required and the extent of deuteration necessary to see an effect on metabolism, if any, will be different for each compound.

Unless otherwise stated, when a position is designated specifically as "H" or "hydrogen," the position is understood to have hydrogen at its natural abundance isotopic composition. Also unless otherwise stated, when a position is designated specifically as "D" or "deuterium," the position is understood to have deuterium at an abundance that is at least 3000 times greater than the natural abundance of deuterium, which is 0.015% (i.e., the term "D" or "deuterium" indicates at least 45% incorporation of deuterium).

The term "isotopic enrichment factor" as used herein means the ratio between the isotopic abundance of D at the specified position in a compound of this invention and the naturally occurring abundance of that isotope.

Increasing the amount of deuterium present in a compound (e.g., a compound of Formula (I) is called "deuterium-enrichment," and such compounds are referred to as "deuterium-enriched" compounds. If not specifically noted, the percentage of enrichment refers to the percentage of deuterium present in the compound.

In other embodiments, a compound of this invention has an isotopic enrichment factor for each deuterium present at a site designated at a potential site of deuteration on the compound of at least 3500 (52.5.% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6466.7 (97% deuterium incorporation), at least 6633.3 (99.5% deuterium incorporation). It is understood that the isotopic enrichment factor of each deuterium present at a site designated as a site of deuteration is independent of other deuterated sites. For example, if there are two sites of deuteration on a compound one site could be deuterated at 52.5% while the other could be deuterated at 75%. The resulting compound would be considered to be a compound wherein the isotopic enrichment factor is at least 3500 (52.5%).

In some embodiments, the compounds of Formula (I), (II), or (III) comprise an amount of deuterium-enrichment that is more than the amount of deuterium-enrichment present in naturally occurring compounds.

All percentages given for the amount of deuterium present are mole percentages.

It can be difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enriched can be achieved by either exchanging protons with deuterium or by synthesizing the molecule with enriched starting materials.

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

Pharmaceutical Compositions

Pharmaceutical compositions containing compounds described herein such as a compound of Formula (I), (II), or (III) or pharmaceutically acceptable salt thereof can be used to treat or ameliorate a disorder described herein, for example, a disorder responsive to the inhibition of the TRPA1 ion channel in subjects (e.g., humans and animals).

The amount and concentration of compounds of Formula (I), (II), or (III) in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

While it is possible for a compound disclosed herein to be administered alone, it is preferable to administer the compound as a pharmaceutical formulation, where the compound is combined with one or more pharmaceutically acceptable diluents, excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar, (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

The tablets, and other solid dosage forms of the pharmaceutical compositions disclosed herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The formulations disclosed herein can be delivered via a device. Exemplary devices include, but are not limited to, a catheter, wire, stent, or other intraluminal device. Further exemplary delivery devices also include a patch, bandage, mouthguard, or dental apparatus. Transdermal patches have the added advantage of providing controlled delivery of a compound disclosed herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, drops, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parenterally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

One specific embodiment is an antitussive composition for peroral administration comprising an agent that inhibits both a TRPA1-mediated current with an $IC_{50}$ of 1 micromolar or less, and an orally-acceptable pharmaceutical carrier in the form of an aqueous-based liquid, or solid dissolvable in the mouth, selected from the group consisting of syrup, elixer, suspension, spray, lozenge, chewable lozenge, powder, and chewable tablet. Such antitussive compositions can include one or more additional agents for treating cough, allergy or asthma symptom selected from the group consisting of: antihistamines, 5-lipoxygenase inhibitors, leukotriene inhibitors, H3 inhibitors, β-adrenergic receptor agonists, xanthine derivatives, α-adrenergic receptor agonists, mast cell stabilizers, expectorants, and NK1, NK2 and NK3 tachykinin receptor antagonists.

Still another embodiment is a metered dose aerosol dispenser containing an aerosol pharmaceutical composition for pulmonary or nasal delivery comprising an agent that inhibits a TRPA1-mediated current with an $IC_{50}$ of 1 micromolar or less. For instance, it can be a metered dose inhaler, a dry powder inhaler or an air-jet nebulizer.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular, intrathecal and subcutaneous doses of the compounds of this invention for a patient will range from about 0.0001 to about 100 mg per kilogram of body weight per day. For example, the dose can be 1-50, 1-25, or 5-10 mg/kg.

If desired, the effective daily dose of the active compound may be administered as two, three, four, five, six or more sub-doses administered separately at appropriate intervals throughout the day, optionally, in unit dosage forms.

Methods of Treatment

The compounds described herein can be used to treat or prevent a disorder described herein. For example, compounds with TRPA1 inhibitory activity are provided herein for the prevention, treatment, or alleviating symptoms of a disease or condition associated with TRPA1. Compounds of Formula (I), (II), or (III), or pharmaceutical compositions containing one or more compounds of Formula (I), (II), or (III), can be administered to treat disorders, conditions, or diseases described herein such as those treatable by the inhibition of TRPA1. For example, the pharmaceutical compositions comprising compounds of Formula (I), (II), or (III), or pharmaceutically acceptable salts thereof, are useful as a perioperative analgesic, for example in the management of mild to moderate acute post-operative pain and management of moderate to severe acute pain as an adjunct to opioid analgesics. The pharmaceutical compositions comprising a therapeutically-effective dose of compounds of Formula (I), (II), or (III), can be administered to a patient for treatment of pain in a clinically safe and effective manner, including one or more separate administrations of the pharmaceutical compositions comprising compounds of Formula (I), (II), or (III). Additional exemplary methods include the treatment of peripheral diabetic neuropathy (PDN) and chemotherapy induced peripheral neuropathy (CIPN). For example, a pharmaceutical composition comprising a therapeutically effective dose of compounds of Formula (I) (II), or (III), or pharmaceutically acceptable salts thereof can be administered (e.g., intravenously) to a subject in need thereof multiple times per day (e.g., BID) over a course of treatment of one or more days to treat pain in the subject. Pharmaceutical compositions comprising compounds of Formula (I), (II), or (III) can also be used to treat or ameliorate respiratory conditions, such as obstructive diseases, e.g., chronic obstructive pulmonary disease (COPD), asthma (e.g., cold induced asthma, exercise-induced asthma, allergy-induced asthma, and occupational asthma), and cough.

Those of skill in the treatment of diseases linked to the mediation of the TRPA1 receptor will be able to determine the therapeutically effective amount of a compound of Formula (I), (II), or (III) from the test results presented hereinafter. In general, a suitable daily dose of a compound of the invention will be that amount of the compound that is the lowest dose able to produce a therapeutic effect. Such an effective dose will generally depend upon various factors. Generally, oral, sublingual, rectal, intravenous, topical, transdermal, inhaled and intracerebroventricular doses of the compounds of this invention for a patient will range from about 0.0001 to about 100 mg per kilogram of body weight per day. For example, the dose can be 1-50, 1-25, or 5-10 mg/kg. It is contemplated, for instance, that a therapeutically effective dose will be from about 0.001 mg/kg to about 50 mg/kg per kg of body weight, more preferably from about 0.01 mg/kg to about 10 mg/kg per kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

The exact dosage and frequency of administration depends on the particular compound of formula (I), (II), or (III) used, the particular condition being treated, the severity of the condition being treated, the age, weight and general physical condition of the particular patient as well as the other medication the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines. A physician or veterinarian having ordinary skill in the art can readily determine and prescribe the effective amount of the pharmaceutical composition required.

Exemplary disorders suitable for treatment with a compound or composition described herein are provided below.

Pain

The compounds of Formula (I), (II), or (III) that are useful in the modulation of TRPA1 can be used in the formulation of analgesic pharmaceuticals suitable for the treatment and/or prophylaxis of pain in mammals, especially in humans. Endogenous activators of TRPA1 are produced during many pathological conditions including tissue injury, inflammation, and metabolic stress. Compounds and pharmaceutical compositions of the present invention can be administered to treat pain resulting from activation of TRPA1 including neuropathic pain. Relevant neuropathic pain conditions include, but are not limited to, painful diabetic neuropathy, chemotherapy-induced peripheral neuropathy, lower back pain, trigeminal neuralgia, post-herpetic neuralgia, sciatica, and complex regional pain syndrome Compositions and methods provided herein may also be used in connection with treatment of in the treatment of inflammation and inflammatory pain. Such disorders include rheumatoid arthritis, osteoarthritis, temperomandibular disorder. In some embodiments, the compositions and methods provided herein may be used to treat headache pain, e.g., migraine.

Disclosed compounds also may be useful in the treatment of visceral pain and inflammation. Relevant diseases include pancreatitis, inflammatory bowel disease, colitis, Crohn's disease, endometriosis, pelvic pain, and angina.

Additional exemplary pain indications for which compounds disclosed herein can be used include temperomandibular disorder, cancer pain (resulting either from the underlying disease or from the treatments), burn pain, oral pain, oral pain due to cancer treatment, crush and injury induced pain, incisional pain, bone pain, sickle cell disease pain, fibromyalgia and musculoskeletal pain. TRPA1 has been show to play a role in cancer related pain (See, e.g., Trevisan et al., Cancer Res Mar. 11, 2013.); postoperative pain (See, e.g., Wei et al, Anasthesiology, V 117, No. 1 (2012); pathological pain (See, e.g., Chen et al, Pain (2011).); and pain related to chemical injury (See, e.g., Macpherson et al, The Journal of Neuroscience, Oct. 17, 2007 27(42):11412-11415).

Hyperalgesia (e.g., mechanical hyperalgesia, cold hyperalgesia) or increased sensitivity to pain (e.g., acute, chronic). Multiple Chemical Sensitivity is a disorder linked to chemical exposure with multi-organ symptoms including respiratory symptoms and headache.

Allodynia (e.g., cutaneous allodynia, e.g., cephalic, extracephalic) is a pain due to a stimulus which does not normally provoke pain, e.g., temperature or physical stimuli, and differs from hyperalgesia, which generally refers to an extreme, exaggerated reaction to a stimulus which is normally painful.

Migraine

The compounds of Formula (I), (II), or (III) that are useful in the modulation of TRPA1 can be used in the formulation of pharmaceuticals suitable for the treatment and/or prophylaxis of migraine in mammals, especially in humans. Exposure to TRPA1 activators has been shown to trigger migraine in susceptible populations. Such activators include but are not limited to umbellulone, nitroglycerin, cigarette smoke, and formaldehyde. Accordingly, TRPA1 antagonists of the invention represent a significant possible therapeutic for the treatment of both chronic and acute migraine.

Inflammatory Diseases and Disorders

Compositions and methods provided herein may also be used in connection with treatment of inflammatory diseases. These diseases include but are not limited to asthma, chronic obstructive pulmonary disease, rheumatoid arthritis, osteoarthritis, inflammatory bowel disease, glomerulonephritis, neuroinflammatory diseases such as multiple sclerosis, and disorders of the immune system. TRPA1 has been show to play a role in pancreatic pain and inflammation (See, e.g., Schwartz et al., Gastroenterology. 2011 April; 140(4): 1283-1291.).

Peripheral neuropathy, for example diabetic neuropathy, is a particular condition that involves both a neuronal and an inflammatory component. Without being bound by a mechanistic theory, the TRPA1 antagonists of the invention may be useful in treating peripheral neuropathies including, but not limited to, diabetic neuropathy. In addition to their use in the treatment of peripheral neuropathies (e.g., reducing inflammation), the subject inhibitors may also be useful in reducing the pain associated with peripheral neuropathy. TRPA1 has been show to play a role in neuropathy and neuropathic pain (See, e.g., Wei et al, Anesthesiology 2009; 111:147-54; and Koivisto et al., Pharmacological Research 2011.).

Neurogenic inflammation often occurs when neuronal hyperexcitability leads to the release of peptides that trigger inflammation. These peptides include substance P and CGRP. Blocking TRPA1 would reduce neuronal activity and thus could block neurogenic inflammation. For example, neurogenic inflammation in the respiratory tract, can result in asthma and allergic rhinitis symptoms, and neurogenic inflammation in the dura may also mediate migraine pain.

Pancreatitis

Pancreatitis is an inflammation of the pancreas. The pancreas is a large gland behind the stomach and close to the duodenum. Normally, digestive enzymes do not become active until they reach the small intestine, where they begin digesting food. But if these enzymes become active inside the pancreas, they start "digesting" the pancreas itself. TRPA1 has been show to play a role in pancreatic pain and inflammation (See, e.g., Schwartz et al., Gastroenterology. 2011 April; 140(4): 1283-1291.).

Acute pancreatitis is usually, although not exclusively, caused by gallstones or by alcohol abuse. Acute pancreatitis usually begins with pain in the upper abdomen that may last for a few days. The pain may be severe and may become constant. The pain may be isolated to the abdomen or it may reach to the back and other areas. Sometimes, and for some patients, the pain is sudden and intense. Other times, or for other patients, the pain begins as a mild pain that worsens after eating. Someone with acute pancreatitis often looks and feels very sick. Other symptoms may include swollen and tender abdomen, nausea, vomiting, fever, and rapid pulse. Severe cases of acute pancreatitis may cause dehydration and low blood pressure, and may even lead to organ failure, internal bleeding, or death.

During acute pancreatitis attacks, the blood levels of amylase and lipase are often increased by at least 3-fold. Changes may also occur in blood levels of glucose, calcium, magnesium, sodium, potassium, and bicarbonate.

The current treatment depends on the severity of the attack. Treatment, in general, is designed to support vital bodily functions, manage pain, and prevent complications. Although acute pancreatitis typically resolved in a few days, pain management during an attack is often required. The compounds disclosed herein can be used to relieve the pain associated with acute pancreatitis.

Chronic pancreatitis may develop if injury to the pancreas continues. Chronic pancreatitis occurs when digestive enzymes attack and destroy the pancreas and nearby tissues, causing scarring and pain. Chronic pancreatitis may be caused by alcoholism, or by blocked, damaged, or narrowed pancreatic ducts. Additionally, hereditary factors appear to influence the disease, and in certain cases, there is no identifiable cause (so called idiopathic pancreatitis).

Most people with chronic pancreatitis have abdominal pain. The pain may get worse when eating or drinking, spread to the back, or become constant and disabling. Other symptoms include nausea, vomiting, weight loss, and fatty stools.

Relieving pain is the first step in treating chronic pancreatitis. Once the pain has been managed, a high carbohydrate and low fat dietary plan is put in place. Pancreatic enzymes may be used to help compensate for decrease enzyme production from the injured pancreas. Sometimes insulin or other drugs are needed to control blood glucose.

Although pain is typically managed using drug therapy, surgery may be necessary to relieve pain. Surgery may be necessary to drain an enlarged pancreatic duct or even to removing a portion of a seriously injured pancreas.

Pain is frequently present with chronic pancreatitis. For example, pain is present for approximately 75% of patients with alcoholic chronic pancreatitis, 50% of patients with late onset idiopathic chronic pancreatitis, and 100% of patients with early-onset idiopathic chronic pancreatitis (DiMagno, 1999, Gastroenterology 116(5): 1252-1257).

A minority of patients with pain have readily identifiable lesions which are relatively easy to treat surgically or endoscopically. In other patients, pain is often thought to result from a variety of causes, including elevated intrapancreatic pressure, ischemia, and fibrosis. Without being bound by theory, however, these phenomena are not likely the underlying cause of the pain. Rather, pain may result from a background of neuronal sensitization induced by damage to the perineurium and subsequent exposure of the nerves to mediators and products of inflammation.

Given the importance of effective pain management in patients with chronic pancreatitis, additional therapies for treating painful symptoms are important and useful. The compounds disclosed herein can be used to manage the pain associated with chronic pancreatitis; they can be used alone or as part of an overall therapeutic treatment plan to manage patients with chronic pancreatitis. For example, the compounds can be administered with pancreatic enzymes and/or insulin as part of a therapeutic regimen designed to manage patients with chronic pancreatitis.

Cancer treatments are not only painful, but they may even be toxic to healthy tissue. Some chemotherapeutic agents can cause painful neuropathy. Accordingly, the compounds disclosed herein could represent a significant possible therapeutic for the treatment of the pain and/or inflammation associated with cancer treatments that cause neuropathy.

A major function of prostaglandins is to protect the gastric mucosa. Included in this function is the modulation of intracellular calcium level in human gastric cells which plays a critical role in cell proliferation. Consequently, inhibition of prostaglandins by nonsteroidal anti-inflammatory drugs (NSAIDs) can inhibit calcium influx in gastric cells (Kokoska et al. (1998) Surgery (St Louis) 124 (2):429-437). The NSAIDs that relieve inflammation most effectively also produce the greatest gastrointestinal damage (Canadian Family Physician, 5 Jan. 1998, p. 101). Thus, the ability to independently modulate calcium channels in specific cell types may help to alleviate such side effect of anti-inflammatory therapy. Additionally or alternatively, administration of TRPA1 inhibitory compounds disclosed herein may be used in combination with NSAIDs, thus promoting pain relief using reduced dosage of NSAIDs.

TRPA1 may mediate ongoing nociception in chronic pancreatitis; and may be involved in transforming acute into chronic inflammation and hyperalgesia in pancreatitis. TRPA1 may also mediate irritation and burning in the e.g., nasal and oral mucosa and respiratory lining.

Neuropathy

Because TRPA1 overactivity can lead to a toxic calcium overload, TRPA1 antagonists also have utility in the prevention of neuropathy associated with diabetes, chemical injury, chemotherapy, medicines such as statins, HIV/AIDS, Fabry's disease, vitamin deficiency, inherited polyneuropathy such as Marie-Charcot Tooth disease, and trauma. Peripheral neurodegenerative diseases such as Amyotrophic Lateral Sclerosis may also be amenable to treatment with a TRPA1 antagonist.

Pulmonary Disease and Cough

Compositions and methods provided herein may also be used in connection with the treatment of pulmonary diseases, including, but not limited to, asthma (including exercise-induced asthma, atopic asthma, allergic asthma), Chronic Obstructive Pulmonary disease (COPD, emphysema,) cystic fibrosis, bronchiectasis, bronchiolitis, allergic bronchopulmonary aspergillosis, bronchiolitis obliterans (popcorn worker lung), diseases due to chemical exposure including exposures to diacetyl, formaldehyde, and other irritants. These conditions also include tuberculosis, restrictive lung disease including asbestosis, radiation fibrosis, hypersensitivity pneumonitis, infant respiratory distress syndrome, idiopathic pulmonary fibrosis, idiopathic interstitial pneumonia sarcoidosis, eosinophilic pneumonia, lymphangioleiomyomatosis, pulmonary Langerhan's cell histiocytosis, and pulmonary alveolar proteinosis; respiratory tract infections including upper respiratory tract infections (e.g., common cold, sinusitis, tonsillitis, pharyngitis and laryngitis) and lower respiratory tract infections (e.g., pneumonia); respiratory tumors whether malignant (e.g., small cell lung cancer, non-small cell lung cancer, adenocarcinoma, squamous cell carcinoma, large cell undifferentiated carcinoma, carcinoid, mesothelioma, metastatic cancer of the lung, metastatic germ cell cancer, metastatic renal cell carcinoma) or benign (e.g., pulmonary hamartoma, congenital malformations such as pulmonary sequestration and congenital cystic adenomatoid malformation (CCAM)); pleural cavity diseases (e.g., empyema and mesothelioma); and pulmonary vascular diseases, e.g., pulmonary embolism such as thromboembolism, and air embolism (iatrogenic), pulmonary arterial hypertension, pulmonary edema, pulmonary hemorrhage, inflammation and damage to capillaries in the lung resulting in blood leaking into the alveoli. Other conditions that may be treated include disorders that affect breathing mechanics (e.g., obstructive sleep apnea, central sleep apnea, Guillan-Barre syndrome, and myasthenia gravis).

The present compounds can also be useful for treating, reducing, or preventing cough (with or without the production of sputum), cough associated with asthma, cough associated with influenza, coughing blood (haemoptysis), cough of unknown etiology, and cough due to chemical exposures.

Dermatological Disorders

A number of agents that cause itch activate TRPA1 directly or via activation of receptors which couple to TRPA1 downstream. Compositions and methods provided herein may also be used in connection with the treatment of itch. Indications include, but are not limited to, conditions triggered by exposure to exogenous chemicals such as contact dermatitis, poison ivy, itch due to cancer including lymphomas, itch caused by medications such as chloroquine, itch due to reactive drug metabolites or itch due to dry skin.

Additional exemplary indications include atopic dermatitis, psoriasis, hives, eczema, dyshidrotic eczema, mouth ulcers, diaper rash.

Itch

Itch, or acute pruritus, while serving an important protective function by e.g., warning against harmful agents in the environment, it can also be a debilitating condition that e.g., accompanies numerous skin, systemic and nervous system disorders. Some forms of itch are mediated by histamine signaling as such are susceptible to treatment with e.g., antihistamines. However, most pathophysiological itch conditions are insensitive to antihistamine treatment. Compounds and pharmaceutical compositions of the present invention can be administered to treat itch.

Atopic dermatitis (AD) is a chronic itch and inflammatory disorder of the skin. Patients with severe AD can develop asthma and allergic rhinitis, also known as atopic march. Skin rash and pruritus may be associated with atopic disease. Chronic itch, e.g., in AD and psoriasis; includes pathophysiological hallmarks such as robust scratching, extensive epidermal hyperplasia from e.g., eczema, kidney failure, cirrhosis, nervous system disorders, some cancers.

Allergic contact dermatitis is a common skin disease associated with inflammation and persistent pruritus.

Methods as disclosed herein may inhibit skin edema, keratinocyte hyperplasia, nerve growth, leukocyte infiltration, and antihistamine-resistant scratching behavior. Methods as disclosed herein may inhibit allergic response to e.g., exogenous stimulants, e.g., haptens, oxazolone, urushiol (e.g., from poison ivy).

Disease and Injury Models

Compounds that antagonize TRPA1 function may be useful in the prophylaxis and treatment of any of the foregoing injuries, diseases, disorders, or conditions. In addition to in vitro assays of the activity of these compounds, their efficacy can be readily tested in one or more animal models. There are numerous animal models for studying pain. The various models use various agents or procedures to simulate pain resulting from injuries, diseases, or other conditions (Blackburn-Munro (2004) Trends in Pharmacological Sciences 25: 299-305 (see, for example, Tables 1, 3, or 4)). Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the models described in the Trevisan model, and the Koivisto references including Streptozotocin induced painful diabetic neuropathy, bortezomib induced peripheral neuropathy and oxaliplatin induced peripheral neuropathy; the Chung model, the spared nerve injury model, the carageenan induced hyperalgesia model, the complete Freund's adjuvant induced hyperalgesia model, the thermal injury model, the formalin model and the Bennett Model.

In the Trevisan reference, chemotherapy-induced peripheral neuropathy model involves the induction if a CIPN phenotype in mice by treatment with bortezomib or oxaliplatin (Trevisan et al, Cancer research 73, 3120-3131, 2013). Treatment of an animal with an inhibitor of TRPA1 can be evaluated using any of a variety of nociceptive tests such as the Von Frey hair test, the hot plate test, cold simulation, chemical hyperalgesia, or the rotarod test.

The model of peripheral diabetic neuropathy (PDN) in the Koivisto reference involves induction of diabetes mellitus (DM) in rats with streptozotocin, and assessing axon reflex induced by intraplantar injection of a TRPA1 agonist. (Pharmacological Research 2011) Treatment with a compound that inhibits TRPA1 can be evaluated for the reduction in DM-induced attenuation of the cutaneous axon reflex.

The Chung model of neuropathic pain (without inflammation) involves ligating one or more spinal nerves (Chung et al. (2004) Methods Mol Med 99: 35-45; Kim and Chung (1992) Pain 50: 355-363). Ligation of the spinal nerves results in a variety of behavioral changes in the animals including heat hyperalgesia, cold allodynia, and ongoing pain. Compounds that antagonize TRPA1 can be administered to ligated animals to assess whether they diminish these ligation-induced behavioral changes in comparison to that observed in the absence of compound.

Carageenan induced hyperalgesia and complete Freund's adjuvant (CFA) induced hyperalgesia are models of inflammatory pain (Walker et al. (2003) Journal of Pharmacol Exp Ther 304: 56-62; McGaraughty et al. (2003) Br J Pharmacol 140: 1381-1388; Honore et al. (2005) J Pharmacol Exp Ther). Compounds that antagonize TRPA1 can be administered to carrageenan or CFA challenged animals to assess whether they diminish cold, mechanical or heat hypersensitivity in comparison to that observed in the absence of compound. In addition, the ability of compounds that antagonize TRPA1 function to diminish cold and/or mechanical hypersensitivity can also be assessed in these models. Typically, the carrageenan induced hyperalgesia model is believed to mimic acute inflammatory pain and the CFA model is believed to mimic chronic pain and chronic inflammatory pain.

Exemplary models of inflammatory pain include the rat model of intraplantar bradykinin injection. Briefly, the baseline thermal sensitivity of the animals is assessed on a Hargreave's apparatus. TRPA1 blockers are then administered systemically. Bradykinin is subsequently injected into the paw and a hyperalgesia is allowed to develop. Thermal escape latency is then measured at multiple time points over the next few hours (Chuang et al., 2001; Vale et al., 2004).

Inflammation is often an important contributing factor to pain. As such, it is useful to identify compounds that act as anti-inflammatories. Many compounds that reduce neural activity also prevent neurogenic inflammation. To measure inflammation directly, the volume of a rat paw can be assessed using a plethysmometer. After baseline measurement is taken, carrageenan can be injected into the paw and the volume can be monitored over the course of hours in animals that have been treated with vehicle or drug. Drugs that reduce the paw swelling are considered to be anti-inflammatory.

Migraines are associated with significant pain and inability to complete normal tasks. Several models of migraine exist including the rat neurogenic inflammation model, (see Buzzi et al (1990) Br J Pharmacol; 99:202-206), and the Burstein Model (see Strassman et al., (1996) Nature 384: 560-564).

The Bennett model uses prolonged ischemia of the paw to mirror chronic pain (Xanthos et al. (2004) J Pain 5: S1). This provides an animal model for chronic pain including post-operative pain, complex regional pain syndrome, and reflex sympathetic dystrophy. Prolonged ischemia induces behavioral changes in the animals including hyperalgesia to mechanical stimuli, sensitivity to cold, pain behaviors (e.g., paw shaking, licking, and/or favoring), and hyperpathia. Compounds that antagonize TRPA1 can be administered to challenged animals to assess whether they diminish any or all of these behaviors in comparison to that observed in the absence of compound. Similar experiments can be conducted in a thermal injury or UV-burn model which can be used to mimic post-operative pain.

Additional models of neuropathic pain include central pain models based on spinal cord injury. Chronic pain is generated by inducing a spinal cord injury, for example, by dropping a weight on a surgically exposed area of spinal cord (e.g., weight-drop model). Spinal cord injury can additionally be induced by crushing or compressing the spinal cord, by delivering neurotoxin, using photochemicals, or by hemisecting the spinal cord.

Additional models of neuropathic pain include peripheral nerve injury models. Exemplary models include, but are not limited to, the neuroma model, the Bennett model, the Seltzer model, the Chung model (ligation at either L5 or L5/L6), the sciatic cryoneurolysis model, the inferior caudal trunk resection model, and the sciatic inflammatory neuritis model. Id.

Exemplary models of neuropathic pain associated with particular diseases are also available. Diabetes and shingles are two diseases often accompanied by neuropathic pain. Even following an acute shingles episodes, some patients continue to suffer from postherpetic neuralgia and experience persistent pain lasting years. Neuropathic pain caused by shingles and/or postherpetic neuralgia can be studied in the postherpetic neuralgia model (PHN). Diabetic neuropathy can be studied in diabetic mouse models, as well as chemically induced models of diabetic neuropathy.

As outlined above, cancer pain may have any of a number of causes, and numerous animal models exist to examine cancer pain related to, for example, chemotherapeutics or tumor infiltration. Exemplary models of toxin-related cancer pain include the vincristine-induced peripheral neuropathy model, the taxol-induced peripheral neuropathy model, and the cisplatin-induced peripheral neuropathy model. An exemplary model of cancer pain caused by tumor infiltration is the cancer invasion pain model (CIP).

Primary and metastatic bone cancers are associated with tremendous pain. Several models of bone cancer pain exist including the mouse femur bone cancer pain model (FBC), the mouse calcaneus bone cancer pain model (CBC), and the rat tibia bone cancer model (TBC). Id.

An additional model of pain is the formalin model. Like the carrageenan and CFA models, the formalin model involves injection of an irritant intradermally or intraperitoneally into an animal. Injection of formalin, a 37-40% percent solution of formaldehyde, is the most commonly used agent for intradermal paw injection (the formalin test). Injection of a 0.5 to 15 percent solution of formalin (usually about 3.5%) into the dorsal or plantar surface of the fore- or hindpaw produces a biphasic painful response of increasing and decreasing intensity for about 60 minutes after the injection. Typical responses include the paw being lifted, licked, nibbled, or shaken. These responses are considered nociceptive. The initial phase of the response (also known as the Early Phase), which lasts 3 to 5 minutes, is probably due to direct chemical stimulation of nociceptors. This is followed by 10 to 15 minutes during which animals display little behavior suggestive of nociception. The second phase of this response (also known as the Late Phase) starts about 15 to 20 minutes after the formalin injection and lasts 20 to 40 minutes, initially rising with both number and frequency of nociceptive behaviors, reaching a peak, then falling off. The intensities of these nociceptive behaviors are dependent on the concentration of formalin used. The second phase involves a period of sensitization during which inflammatory phenomena occur. The two phases of responsiveness to formalin injection makes the formalin model an appropriate model for studying nociceptive and acute inflammatory pain. It may also model, in some respects, neuropathic pain.

In addition to any of the foregoing models of chronic pain, compounds that antagonize TRPA1 function can be tested in one or more models of acute pain. Valenzano et al. (2005) Neuropharmacology 48: 658-672. Regardless of whether compounds are tested in models of chronic pain, acute pain, or both, these studies are typically (though not exclusively) conducted, for example, in mice, rats, or guinea pigs. Additionally, compounds can be tested in various cell lines that provide in vitro assays of pain.

Many individuals seeking treatment for pain suffer from visceral pain. Animal models of visceral pain include the rat model of inflammatory uterine pain (Wesselmann et al., (1997) Pain 73:309-317), injection of mustard oil into the gastrointestinal tract to mimic irritable bowel syndrome (Kimball et al., (2005) Am J Physiol Gastrointest Liver Physiol, 288(6):G1266-73), injection of mustard oil into the bladder to mimic overactive bladder or bladder cystitis (Riazimand (2004), BJU 94: 158-163). The effectiveness of a TRPA1 compound can be assessed by a decrease in writhing, gastrointestinal inflammation or bladder excitability.

For testing the efficacy of TRPA1 antagonists for the treatment of cough, experiments using the conscious guinea pig model of cough can be readily conducted (Tanaka and Maruyama (2003) Journal Pharmacol Sci 93: 465-470; McLeod et al. (2001) Br J Pharmacol 132: 1175-1178). Briefly, guinea pigs serve as a useful animal model for cough because, unlike other rodents such as mice and rats, guinea pigs actually cough. Furthermore, guinea pig coughing appears to mimic human coughing in terms of the posture, behavior, and appearance of the coughing animal.

To induce cough, conscious guinea pigs are exposed to an inducing agent such as citric acid or capsaicin. The response of the animal is measured by counting the number of coughs. The effectiveness of a cough suppressing agent, for example a compound that inhibits TRPA1, can be measured by administering the agent and assessing the ability of the agent to decrease the number of coughs elicited by exposure to citric acid, capsaicin, or other similar cough-inducing agent. In this way, TRPA1 inhibitors for use in the treatment of cough can be readily evaluated and identified.

Additional models of cough may also include the unconscious guinea pig model (Rouget et al. (2004) Br J Pharmacol 141: 1077-1083). Either of the foregoing models can be adapted for use with other animals capable of coughing. Exemplary additional animals capable of coughing include cats and dogs.

Compounds of the invention may be tested in multiple models of asthma. One example is the murine ovalbumin model of asthma (Caceres A I et al., Proc Natl Acad Sci USA. 2009 Jun. 2; 106(22):9099-104; Epub 2009 May 19). In this model, ovalbumin is injected into the intraperitoneal cavity several times over 2 weeks. Sometime in the third week, animals are challenged with intranasal ovalbumin an airway hyperresponsiveness, inflammation and inflammatory cytokine production may be measured. Compounds are dosed during the challenge phase of the model. TRPA1 knock-out mice may be substituted into the above models as reported by Caceres et al.

An example of a large animal model of asthma the conscious allergic sheep model as described in Abraham, W. M. et al. may be used to assess effects of compounds on the antigen-induced late stage response of asthma (Abraham W M., Am J Respir Crit Care Med. 2000 August; 162(2 Pt 1):603-11). Briefly, baseline airway responsiveness is measured by plethysmograph in conscious sheep prior to a nebulized administration of *Ascaris suum* extract to induce asthma. After baseline readings are captured, animals are challenged with a nebulized dose of *Ascaris suum*. Antigen sensitivity is determined by decrease in pulmonary flow resistance from baseline. Once animals demonstrate antigen-sensitivity, test compounds may be administered and additional pulmonary flow resistance readings captured to assess changes airway responsiveness. Models in the horse and beagle dog are sometimes also used.

Additional models may include the Brown Norway rat model and the $C_{57}BL/6J$ mouse model of asthma as described in Raemdonck et al. (Raemdonck K et al., Thorax. 2012 January; 67(1):19-25; Epub 2011 Aug. 13). Briefly Brown Norway rats and $C_{57}BL/6J$ mice may be sensitized and challenged with aerosol delivered ovalbumin. Once sensitivity is confirmed by a decrease in lung function as measured by whole body plethysmograph readings, compounds of the invention may be administered. Visual and audible signs of respiratory distress including wheezing may also be present.

Dermatitis

Multiple mouse models of dermatological disease currently exist. For example, Liu et al. describe multiple oxazolone and urushiol-induced contact dermatitis models (Liu B et al., FASEB J. 2013 Sep.; 27(9):3549-63; Epub 2013 May 30). Briefly, Trpa1 knock-out mice receive topical administrations of oxazolone or urushiol to induce dermatitis and itch responses. Epidermis thickness may also be measured by taking ear punches and measurements of challenged areas compared with untreated ears. In vivo treatment compounds may be determined by administering compounds to the animals prior to or after ozazolone or urushiol treatments. Scratching behaviors are recorded by video cameras positioned above observation chambers. Observers blind to treatment groups record the time animals spend scratching over the course of thirty minutes.

An alternative mouse model of dry-skin evoking itch involves administration of acetone, ether, and water to the mouse as reported by Wilson et al. (Wilson S R et al., J Neurosci. 2013 May 29; 33(22):9283-94) In this model, the area to be treated is shaved and mice receive topical administration of acetone and ether twice daily on the area to be observed, e.g. cheek or caudal back. In vivo efficacy of treatment compounds may be determined by administering compounds to the animals prior to or after acetone and ether administration. Scratching behavior is recorded by camera for a period of 20 minutes and quantified by observers blind to treatment groups.

In addition, pruritus may be induced by direct injection of an agent that causes itch. Examples of these agents may be found in Akayimo and Carstens, 2013. Some examples are: chloroquine (Wilson et al., 2011), bile acids, TSLP (Wilson et al., 2013), and IL-31 (Cevikbas et al., 2014). Typically scratching bouts in a defined period are recorded by an observed blinded to treatment group.

Numerous rodent models of incontinence exist. These include models of incontinence induced by nerve damage, urethral impingement and inflammation. Models of urethral impingement include the rat bladder outflow obstruction model. (Pandita, R K, and Andersson K E. Effects of intravesical administration of the K+ channel opener, Z.D6169, in conscious rats with and without bladder outflow obstruction. J Urol 162: 943-948, 1999). Inflammatory models include injection of mustard oil into the bladder.

To test the effectiveness of a TRPA1 inhibitor compound in treating incontinence, varying concentrations of compound (e.g., low, medium, and high concentration) can be administered to rats following surgical partial bladder outlet obstruction (BOO). Efficacy of the varying doses of TRPA1 inhibitory compound can be compared to controls administered excipients alone (sham control). Efficacy can further be compared to rats administered a positive control, such as atropine. Atropine is expected to decrease bladder overactivity following partial bladder outlet obstruction in the BOO model. Note that when testing compounds in the BOO model, compounds can be administered directly to the bladder or urethra (e.g., by catheter) or compounds can be administered systemically (e.g., orally, intravenously, intraperitoneally, etc).

Several rat models of pancreatitic pain have recently been described (Lu, 2003, Anesthesiology 98(3): 734-740; Winston et al., 2003, Journal of Pain 4(6): 329-337). Lu et al. induced pancreatitis by systemic delivery of dibutylin dichloride in rats. Rats showed an increase in withdrawal events after von Frey filament stimulation of the abdomen and decreased withdrawal latency after thermal stimulation during a period of 7 days. The pain state induced in these animals was also characterized by increased levels of substance P in spinal cords (Lu, et al., 2003). To test the efficacy of a TRPA1 inhibitor in this model, a TRPA1 inhibitor can be administered following or concurrently with delivery of dibutylin dichloride. Control animals can be administered a carrier or a known pain reliever. Indicia of pain can be measured. Efficacy of a TRPA1 inhibitor can be evaluated by comparing the indicia of pain observed in animals receiving a TRPA1 inhibitor to that of animals that did not receive a TRPA1 inhibitor. Additionally, efficacy of a TRPA1 inhibitor can be compared to that of known pain medications.

The efficacy of von Frey filament testing as a means to measure nociceptive behavior was also shown by inducing pancreatitis by systemic L-arginine administration (Winston et al, 2003). The efficacy of a TRPA1 inhibitor can similarly be tested following pancreatitis induced by systemic L-arginine administration.

Lu et al. also described direct behavioral assays for pancreatic pain using acute noxious stimulation of the pancreas via an indwelling ductal cannula in awake and freely moving rats. These assays included cage crossing, rearing, and hind limb extension in response to intrapancreatic bradykinin infusion. Intrathecal administration of either D-APV (NMDA receptor antagonist) or morphine alone partially reduced visceral pain behaviors in this model. Combinations of both reduced pain behaviors to baseline. The efficacy of a TRPA1 inhibitor can similarly be tested in this system.

Any of the foregoing animal models may be used to evaluate the efficacy of a TRPA1 inhibitor in treating pain associated with pancreatitis. The efficacy can be compared to a no treatment or placebo control. Additionally or alternatively, efficacy can be evaluated in comparison to one or more known pain relieving medicaments.

EXAMPLES

In Vitro Characterization of Exemplary Compounds of the Invention

Example 1. Method for Measuring Inhibition of the TRPA1 Ion Channel

Compounds of Formula (I), (II), or (III) inhibit the TRPA1 channel, as shown by measuring the in vitro inhibition of human TRPA1, provided in data tables shown in Table 2, using the procedure outlined in del Camino et al., *The Journal of Neuroscience*, 30(45):15165-15174 (Nov. 10, 2010), incorporated herein by reference and summarized below. Data for TRPA1 inhibition was obtained by this method for the indicated compounds of Formula (I), (II), or (III), with the relevant data included in Table 2 below. All currents were recorded in whole-cell configuration using EPC-9 and EPC-10 amplifiers and Patchmaster software (HEKA) or similar. Patch pipettes had a resistance of 1.5-3 MΩ and up to 75% of the series resistance was compensated. The standard pipette solution consisted of 140 mM CsAsp, 10 mM EGTA, 10 mM HEPES, 2.27 mM, 20 $MgCl_2$, 1.91 mM $CaCl_2$, and up to 0.3 mM $Na_2GTP$, with pH adjusted to 7.2 with CsOH. In addition, a solution containing 145 mM CsCl, 10 mM HEPES, 10 mM EGTA, and up to 0.3 mM $Na_2GTP$ and 1 mM $MgCl_2$ (pH 7.2 adjusted with CsOH) can be used. The standard bath solution contained 150 mM NaCl, 10 mM HEPES, 10 mM glucose, 4.5 mM KCl, 1 mM EGTA, 3 mM $MgCl_2$, with pH adjusted to 7.4 with NaOH. In some instances, 2 mM $CaCl_2$ was added in place of EGTA and the concentration of $MgCl_2$ was reduced to 1 mM.

Data were collected either by continuous recordings at −60 mV or by applying voltage ramps from a holding potential of −40 mV every 4 s. Continuous recordings were collected at 400 Hz and digitally filtered off-line at 10 Hz for presentation. Voltage ramps were applied from −100 mV or −80 mV to +100 mV or +80 mV over the course of 400 ms, and data were collected at 10 kHz and filtered at 2.9 kHz. Inward and outward currents were analyzed from the ramps at −80 and 80 mV, respectively. Liquid junction potential correction was not used.

Solutions were switched using a gravity-fed continuous focal perfusion system. To achieve rapid temperature changes, two temperature control, and perfusion systems were employed simultaneously. For temperatures greater than or equal to 22° C., a Warner Instruments bipolar temperature controller (TC-344B) and inline heater (SHM-8) were used. For temperatures below 22° C. a Warner Instruments temperature controller (CL-100) and thermal cooling module (TCM-1) were used. Temperatures were confirmed using a thermistor (Warner Instruments, TA-29), with temperatures at the recorded cell estimated to be within +/−2° C. of those reported.

The antagonist effects of compounds of Formula (I), (II), or (III) against human TRPA1 ("hTRPA1") in a whole cell patch configuration were evaluated using the in vitro assay described above. The current activation tested was 10 μM AITC, and the tested concentrations ranged from 320 pM to 3.2 μM.

Compounds of the invention were also tested for solubility in Normal Ringer Solution. Briefly, compound solubility was determined by dissolving a standard range of volumes of 10 mM DMSO stock of compounds in Normal Ringer Solution (pH 7.4 at room temperature). Following vortex and incubation for 40 minutes at room temperature, solutions were filtered, quenched with acetonitrile, and analyzed by Liquid Chromatography. Solubility limits were determined by comparison to a standard curve. The solubility limit was determined to be greater than 31.3 μM. Solubility is reported as "greater than" if the observed increase between the last 2 dilutions tested is greater than 2-fold.

Table 2 shows the solubility values and hTRPA1 $IC_{50}$ values achieved for the compounds tested.

TABLE 2

Antagonist effects of Compounds against human TRPA1

| Compound # | hTRPA1 $IC_{50}$ (nM) | Solubility (μM) |
|---|---|---|
| 100 | >10000 | >31.3 |
| 101 | 559 | >31.3 |
| 102 | 172 | >31.3 |
| 103 | 47.6 | >31.3 |
| 104 | 7090 | >31.3 |
| 105 | 566 | >31.3 |
| 106 | — | >31.3 |
| 107 | — | >31.3 |

In Vivo Efficacy of Exemplary Compounds of the Invention

Example 2. Formalin Model

Exemplary compounds of the invention can be tested in the formalin-induced pain test reported by Dubuisson et al., Pain 1977 December; 4(2):161-74 (incorporated herein by reference in its entirety).

Example 3. General Experimental Procedures

General Procedures

All reactions were run under an inert atmosphere, generally nitrogen. All non-aqueous reactions were run using solvents. All reactions were stirred either with a magnetic stir bar or with overhead mechanical stirring. All saturated extraction solutions are assumed to be aqueous (saturated $NH_4Cl$ for example). Drying organic solutions with a drying agent implies that the drying agent was removed from the organic solution by filtration. Chromatography refers to column chromatography on silica gel. Preparative thin layer chromatography (TLC) was run plates. Concentration of reaction mixtures implies concentration under reduced pressure and the use of a rotary evaporation instrument. Drying of final products implies drying under high vacuum conditions. Sonication implies the use of an ultrasonic bath. All $^1$H-NMR data were obtained at 400 MHz. Mass spectra were obtained in positive ion mode and are reported as the protonated species $MH^+$. LCMS were performed on a SHIMADZU LCMS-2010EV instrument (Chromolith Sdee-dROP, RP-18e column. 50×4.6 mm. mobile phase: Solvent A: $CH_3CN/H_2O/HCOOH$=10/90/0.05. Solvent B: $CH_3CN/H_2O/HCOOH$=90/10/0.05. 0.8 min@10% B. 2.7 min gradient (10-95% B), then 0.8 min@95% B. Flow rate: 3 mL/min. temperature: 40° C.). Preparative HPLC was performed either on a SHIMADZU LC-8A instrument. (Column: YMC Pack ODS-A (150*30 mm 10 um)) or LC-6AD (column: Shim=Pack PREP-ODS-H (250*20 mm, 10 um)) with UV detection which was controlled by LC solution Chemstation software, with $H_2O$ (0.1% HCOOH) and MeOH ($CH_3CN$) as mobile phase at the indicated flow rate. Chiral HPLC was performed using a CHIRALPAK IB column (150*4.6 mm, 5 um) with the mobile phase comprised of hexanes/EtOH (65/35, 0.8 mL/min, 25 minute run time) at 30° C., using a 15 uL sample injection volume (1 mg/mL in MeOH) and UV detector set at 220/254 nm.

Abbreviations

Bn Benzyl
DCM dichloromethane
DIC N,N'-diisopropylcarbodiimide
DMAP 4-dimethylaminopyridine
DMF N,N-dimethylformamide
DMSO Dimethylsulfoxide
EDC 1-ethyl-3-(3-dimethylaminopropyl)carbodiimide
EA ethyl acetate Ether diethyl ether
h hours
HOAc acetic acid
HOAT 1-hydroxy-7-azabenzotriazole
LAH lithium aluminum hydride
MeOH methanol
min minutes
n-BuLi n-butyllithium
Pd/C palladium on activated carbon, generally 10% palladium load
PE petroleum ether
RT room temperature
S. aq. Saturated aqueous
SEM 2-(trimethylsilyl)ethoxymethyl
TBAI tetrabutylammonium iodide
TEA triethylamine
TFA trifluoroacetic acid
TLC thin layer chromatography
THF tetrahydrofuran Example 4. Synthesis of Compounds 100, 101, 106, and 107

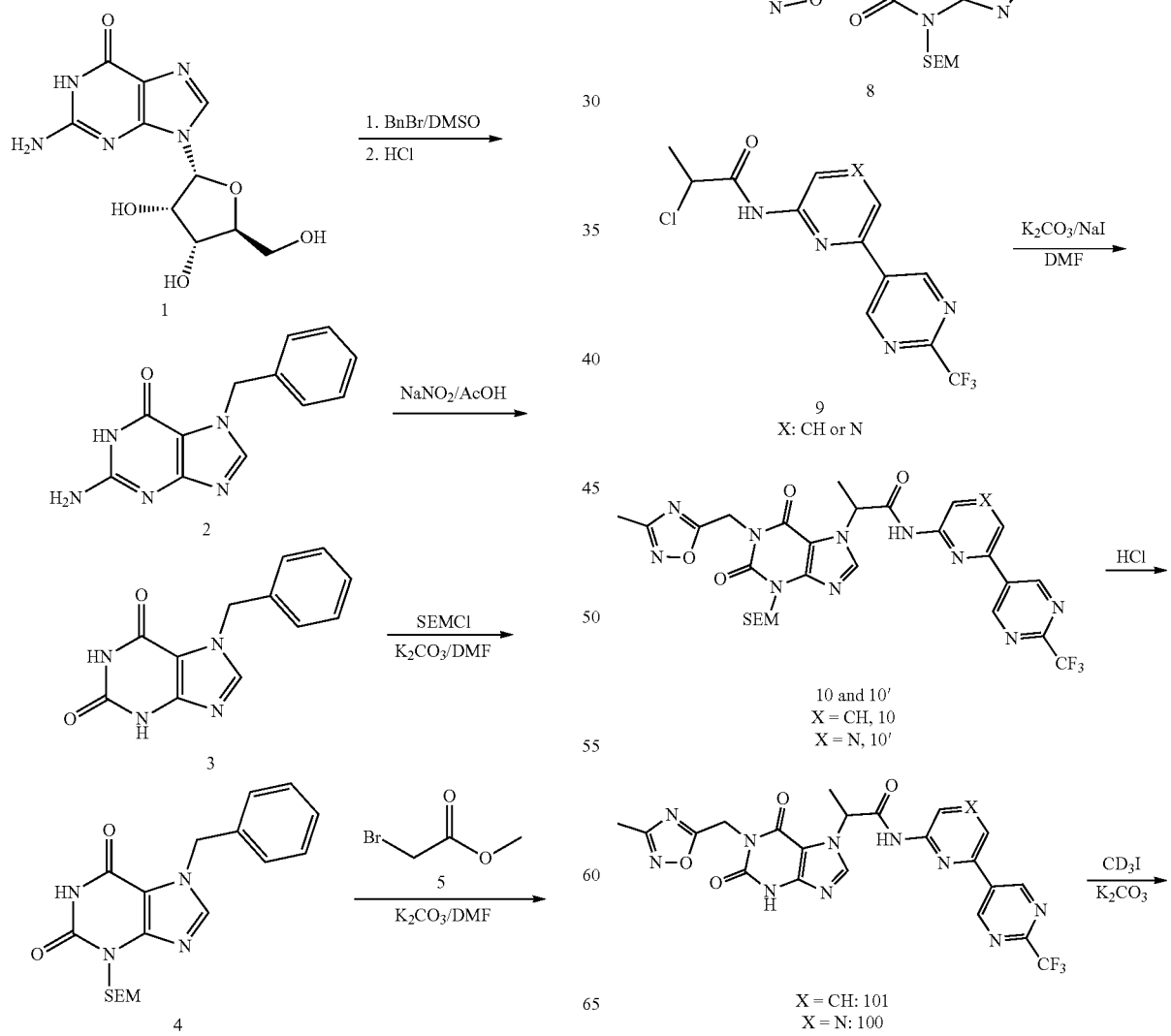

-continued

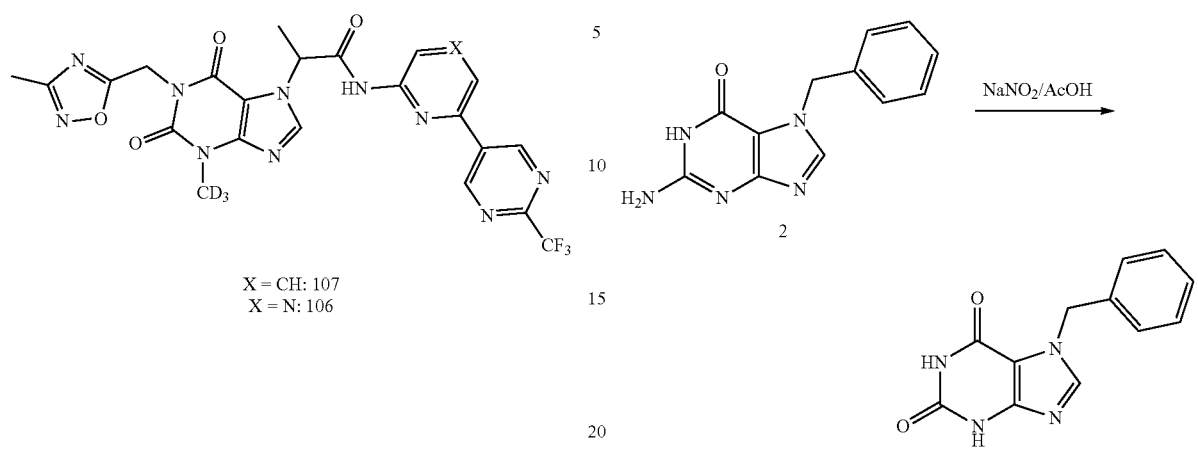

X = CH: 107
X = N: 106

Preparation of Compound 2

Preparation of Compound 3

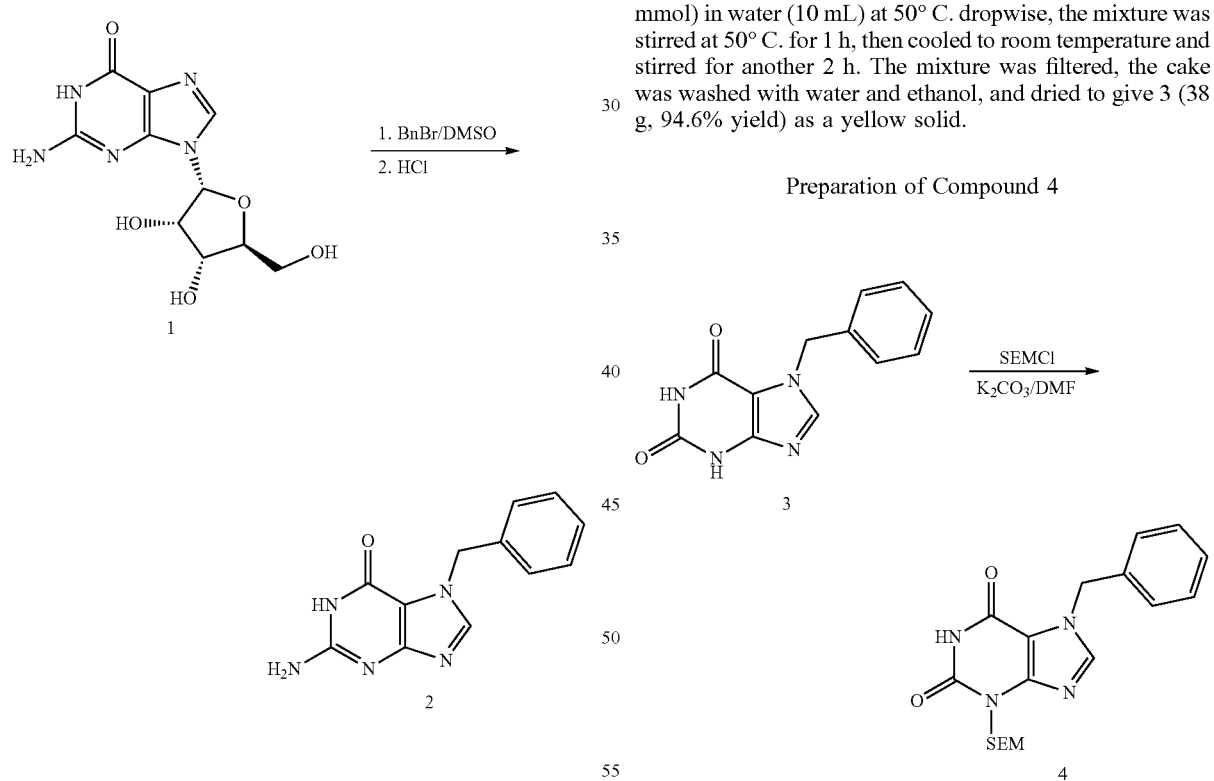

To a solution of 2 (40 g, 166 mmol) in HOAc (480 mL) and water (60 mL) was added sodium nitrite (13.8 g, 200 mmol) in water (10 mL) at 50° C. dropwise, the mixture was stirred at 50° C. for 1 h, then cooled to room temperature and stirred for another 2 h. The mixture was filtered, the cake was washed with water and ethanol, and dried to give 3 (38 g, 94.6% yield) as a yellow solid.

Preparation of Compound 4

To a solution of 1 (84 g, 297 mmol) in DMSO (300 mL) was added benzyl bromide (60 g, 353 mmol). The mixture was stirred at 50° C. overnight. Then the mixture was cooled to room temperature and HCl (300 mL, 2 mol/L) was added and the mixture was stirred at 70° C. for 2 h. The reaction was cooled to room temperature, filtered and cake was washed with water and ethanol, and dried under vacuum to give 2 (55 g, 76.8% yield) as grey solid.

To a solution of 3 (28 g, 115.7 mmol), potassium carbonate (32 g, 232 mmol) in DMF (300 mL) was added SEMCl (19.2 g, 115.7 mmol) at 0° C. dropwise, the reaction was stirred at room temperature overnight after addition. The mixture was poured into ice-water and extracted with EA (100 mL×3), the extracted organic layers were washed with water, brine and dried over anhydrous sodium sulfate, then concentrated, the residue was purified by flash chromatography on silica gel (PE/EA=1:1) to give 4 (15 g, 34.8% yield) as a white solid.

53

Preparation of Compound 6

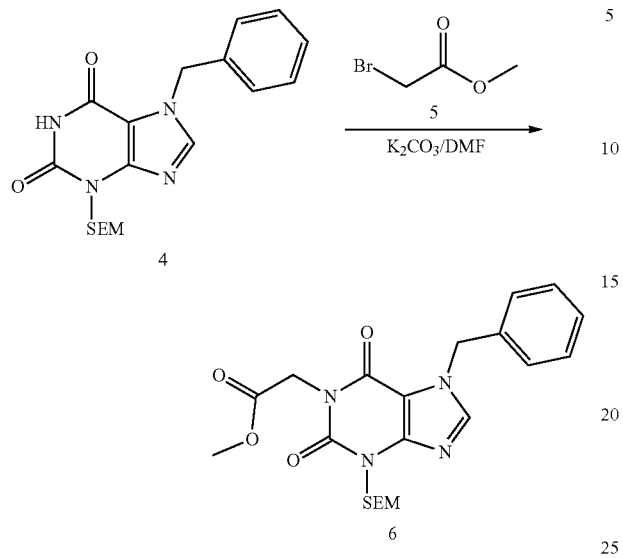

To a solution of 4 (15 g, 40.3 mmol) and potassium carbonate (11.1 g, 80.6 mmol) in DMF (150 mL) was added methyl bromoacetate 5 (12.2 g, 81 mmol), and the mixture was stirred at room temperature overnight. The reaction was poured into water and the precipitate was collected to give 6 (14 g, 78.2% yield) as a white solid, which was used in the next step directly.

Preparation of Compound 7

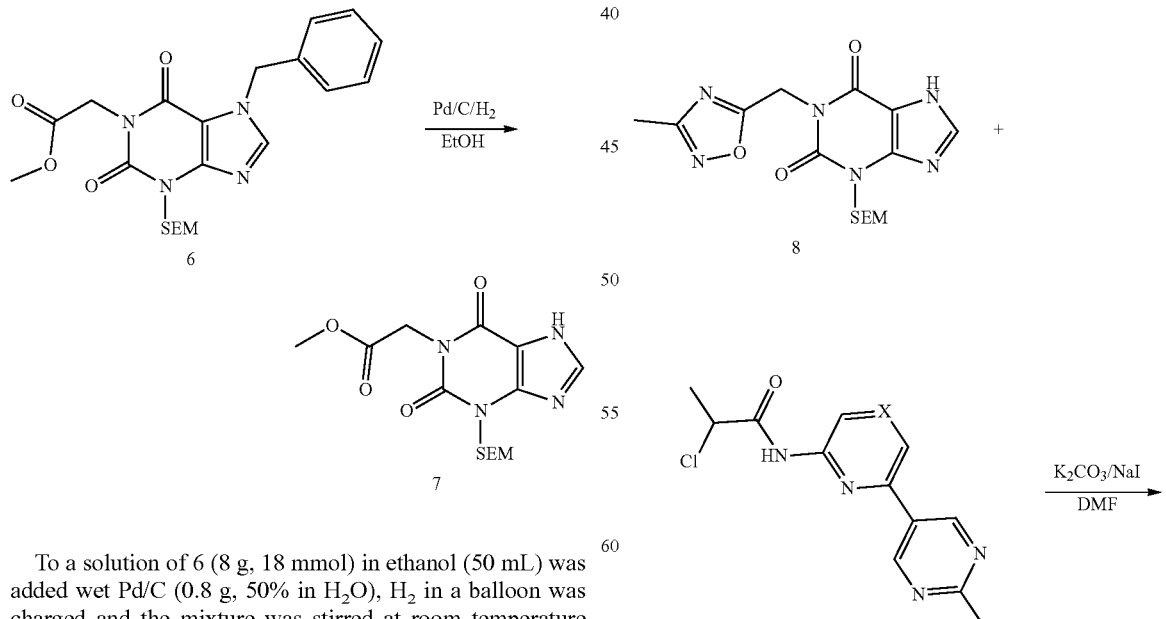

To a solution of 6 (8 g, 18 mmol) in ethanol (50 mL) was added wet Pd/C (0.8 g, 50% in $H_2O$), $H_2$ in a balloon was charged and the mixture was stirred at room temperature under an $H_2$ atmosphere overnight. The reaction was filtered on a pad of celite and concentrated to give desired 7 (5.4 g, 85% yield) as a gray solid, which was used in the next step directly.

54

Preparation of Compound 8

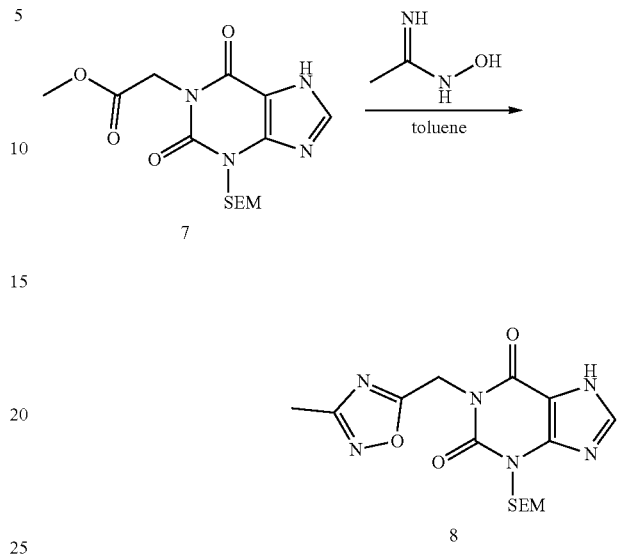

To a solution of 7 (5 g, 14 mmol) in toluene (40 mL) was added N-hydroxyacetimidamide (2.07 g, 28 mmol), and the mixture was stirred at reflux overnight. The reaction was poured into water and extracted with EA (×4), the extracted organic layers were concentrated, and the residue was purified by flash chromatography (EA) on silica gel to give 8 (3 g, 56.7% yield) as a white solid.

Preparation of Compounds 10 and 10'

-continued

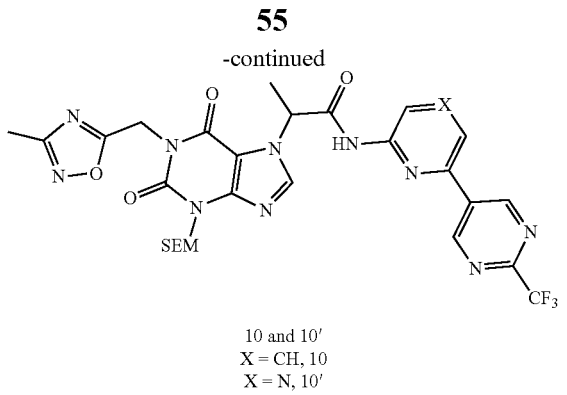

10 and 10'
X = CH, 10
X = N, 10'

To a solution of 8 (1.5 g, 3.97 mmol), 9 (1.0 eq.)(either X=CH or X=N), and potassium carbonate (1.1 g, 8.0 mmol) in DMF (30 mL) was added sodium iodide (1.2 g, 8.0 mmol) and stirred at room temperature overnight. The reaction was quenched with water and extracted with EA (×3), the extracted layers were washed with water, brine, dried over anhydrous sodium sulfate and concentrated, and the residue was purified by flash chromatography on silica gel (PE/EA=1:1) to give 10: 1.5 g, 56.2% yield; or 10': 1.4 g, 52.4% yield) both as a white solid.

Preparation of Compounds 100 and 101

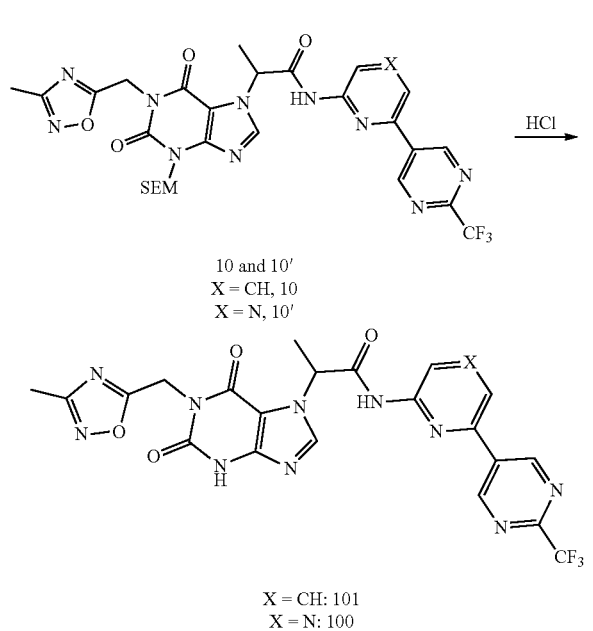

10 and 10'
X = CH, 10
X = N, 10'

X = CH: 101
X = N: 100

To a solution of 10 or 10' (10: 1.5 g, 2.23 mmol; or 10': 1.4 g, 2.08 mmol) in EA (50 mL) was added HCl/EA (2 mol/L, 10 mL). The mixture was stirred at room temperature overnight, then concentrated and the residue was purified by prep-HPLC to give (Compound 101: 0.6 g, 73.8% yield, >95% purity; or Compound 100: 0.9 g, 79.7% yield, >95% purity) both as a white solid.

Analytical data of Compound 101:
$^1$H NMR DMSO-$d_6$ 400 MHz
δ 12.28 (s, 1H), 11.25 (s, 1H), 9.66 (s, 2H), 8.35 (s, 1H), 8.12 (d, J=7.6 Hz, 1H), 8.05-7.98 (m, 2H), 5.79 (d, J=7.2 Hz, 1H), 5.27 (dd, J=24.0 Hz, 16.8 Hz, 2H), 2.26 (s, 3H), 1.88 (d, J=6.8 Hz, 3H);

LCMS (ESI): m/z 543 (M+H)$^+$;
HPLC: >99.9% (254 nm, MeOH), >99.9% (220 nm, MeOH), >99.9% (254 nm, ACN), 99.1% (220 nm, ACN).

Analytical Data of Compound 100:
$^1$H NMR DMSO-$d_6$ 400 MHz
δ 12.32 (s, 1H), 11.64 (s, 1H), 9.70 (s, 2H), 9.35 (s, 1H), 9.23 (s, 1H), 8.38 (s, 1H), 5.80 (d, J=6.4 Hz, 1H), 5.27 (dd, J=22.4 Hz, 16.8 Hz, 2H), 2.26 (s, 3H), 1.90 (d, J=6.8 Hz, 3H);

LCMS (ESI): m/z 544 (M+H)$^+$;
HPLC: 97.7% (254 nm, MeOH), 98.4% (220 nm, MeOH), 97.7% (254 nm, ACN), 97.9% (220 nm, ACN).

Preparation of Compound 106 and Compound 107

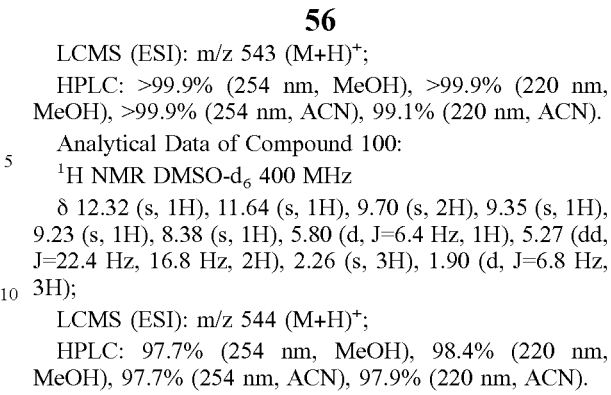

X = CH: 101
X = N: 100

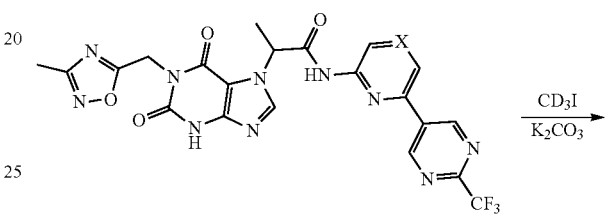

X = CH: 107
X = N: 106

To a solution of (101: 340 mg, 0.63 mmol; or 100: 490 mg, 0.9 mmol) and potassium carbonate (1.2 eq.) in DMF (30 mL) was added CD$_3$I (1.2 eq.), then stirred at room temperature overnight. The mixture was poured into ice water, and the precipitate was collected to give desired product (107: 0.21 g, 59.6% yield, >95% purity; or 106: 0.37 g, 73.4% yield, >95% purity) both as a white solid.

Analytical data of Compound 107:
$^1$H NMR DMSO-$d_6$ 400 MHz
δ 12.28 (s, 1H), 9.66 (s, 2H), 9.34 (s, 1H), 9.23 (s, 1H), 8.47 (s, 1H), 5.82 (s, 1H), 5.84-5.79 (m, 1H), 5.32 (t, J=20.0 Hz, 2H), 2.33 (s, 3H), 1.91 (d, J=7.2 Hz, 3H);

LCMS (ESI): m/z 560 (M+H)$^+$;
HPLC: 96.7% (254 nm, MeOH), 96.9% (220 nm, MeOH), 98.0% (254 nm, ACN), 98.4% (220 nm, ACN).

Analytical data of Compound 106:
$^1$H NMR (DMSO-$d_6$ 400 MHz) δ 11.66 (s, 1H), 9.70 (s, 2H), 9.35 (s, 1H), 9.23 (s, 1H), 8.38 (s, 1H), 5.80 (d, J=6.4 Hz, 1H), 5.27 (dd, J=22.4 Hz, 16.8 Hz, 2H), 2.26 (s, 3H), 1.90 (d, J=6.8 Hz, 3H);

LCMS (ESI): m/z 561 (M+H)$^+$;
HPLC: 99.5% (254 nm, MeOH), 99.7% (220 nm, MeOH), 99.0% (254 nm, ACN), 99.0% (220 nm, ACN).

Example 5. Synthesis of Compounds 102 and 104

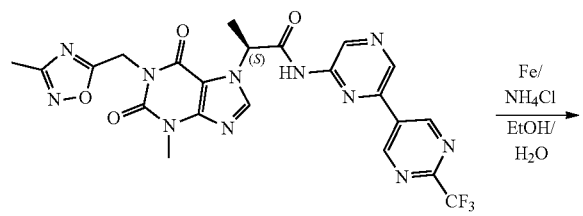

11'

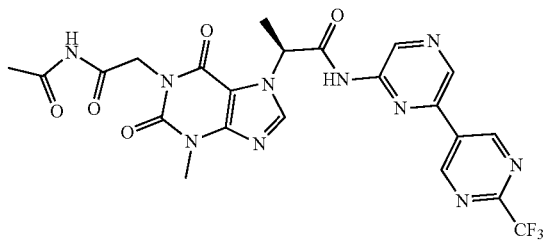

102

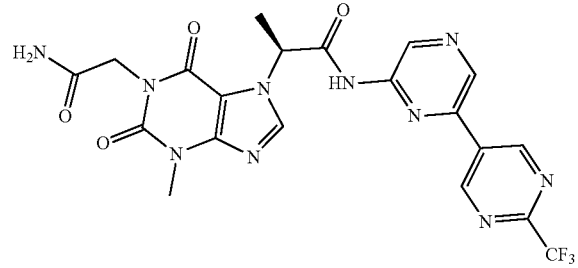

104

To a solution of 11' (1.0 g, 1.8 mmol, synthesized like compound 106 from compound 100, but using CH₃I instead of CD₃I) in EtOH (60 mL) and H₂O (30 mL) was added iron filings (500 mg, 9 mmol) and NH₄Cl (480 mg, 8 mmol), and the suspension was heated at 60° C. and kept stirred for 2 h. The mixture was cooled to room temperature and filtered on a pad of celite, and the filtrate was concentrated under reduced pressure to give a black residue, which was purified by prep-HPLC to give 102 (350 mg, 34.7% yield, >95% purity) and 104 (180 mg, 19.3% yield, >95% purity) both as a white solid.

Analytical data of Compound 102:

¹H NMR DMSO-$d_6$ 400 MHz

δ 11.63 (s, 1H), 11.05 (s, 1H), 9.70 (s, 2H), 9.35 (s, 1H), 8.43 (s, 1H), 5.85-5.80 (m, 1H), 4.77 (dd, J=25.2 Hz, 17.6 Hz, 2H), 3.76 (s, 3H), 2.51 (s, 3H), 1.92 (d, J=7.6 Hz, 3H);

LCMS (ESI): m/z 561 (M+H)⁺;

HPLC: 98.4% (254 nm, MeOH), 98.5% (220 nm, MeOH), 98.4% (254 nm, ACN), 98.6% (220 nm, ACN).

Analytical data of Compound 104:

¹H NMR DMSO-$d_6$ 400 MHz

δ 11.64 (s, 1H), 9.71 (s, 2H), 9.36 (s, 1H), 9.23 (s, 1H), 8.40 (s, 1H), 7.50 (s, 1H), 5.88-5.83 (m, 1H), 4.36 (m, 2H), 3.46 (s, 3H), 1.91 (d, J=7.2 Hz, 3H);

LCMS (ESI): m/z 519 (M+H)⁺;

HPLC: >99.9% (254 nm, MeOH), >99.9% (220 nm, MeOH), >99.9% (254 nm, ACN), >99.9% (220 nm, ACN).

Example 6. Synthesis of Compounds 103 and 105

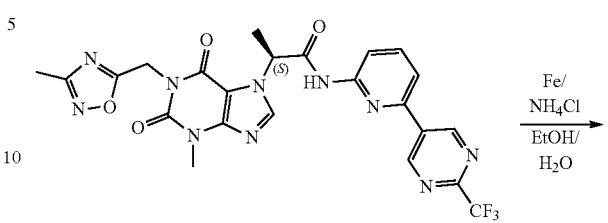

11

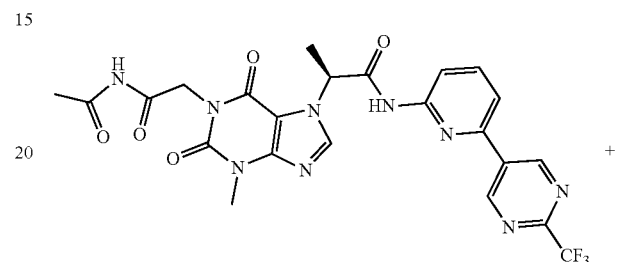

103

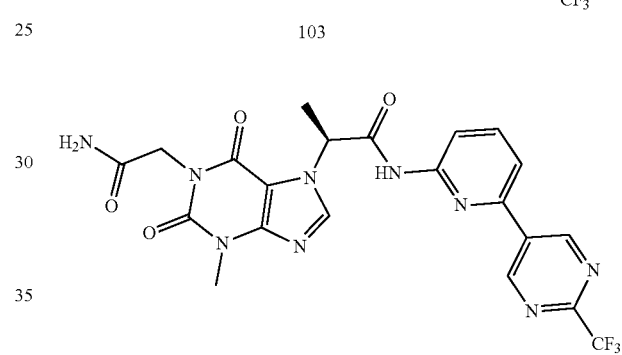

105

Using the same procedure as for the synthesis of compounds 102 and 104, but using 11 as starting material, we obtained 103 (310 mg, 30.8% yield, >95% purity) and 105 (60 mg, 6.4% yield, >95% purity) both as a white solid.

Analytical data of Compound 103:

¹H NMR DMSO-$d_6$ 400 MHz

δ 11.26 (s, 1H), 11.04 (s, 1H), 9.67 (s, 2H), 8.41 (s, 1H), 8.12 (d, J=7.6 Hz, 1H), 8.05-7.98 (m, 2H), 5.83-5.79 (m, 1H), 4.83 (dd, J=27.2 Hz, 17.2 Hz, 2H), 3.47 (s, 3H), 2.12 (s, 3H), 1.90 (d, J=7.2 Hz, 3H);

LCMS (ESI): m/z 560 (M+H)⁺;

HPLC: >99.9% (254 nm, MeOH), >99.9% (220 nm, MeOH), >99.9% (254 nm, ACN), >99.9% (220 nm, ACN).

Analytical data of Compound 105:

¹H NMR DMSO-$d_6$ 400 MHz

δ 11.27 (s, 1H), 9.67 (s, 2H), 8.39 (s, 1H), 8.12 (d, J=7.6 Hz, 1H), 8.05-8.00 (m, 2H), 7.51 (s, 1H), 7.01 (s, 1H), 5.86-5.82 (m, 1H), 4.38-4.36 (m, 2H), 3.46 (s, 3H), 1.89 (d, J=7.2 Hz, 3H);

LCMS (ESI): m/z 518 (M+H)⁺;

HPLC: 95.5% (254 nm, MeOH), 96.4% (220 nm, MeOH), 96.1% (254 nm, ACN), 97.1% (220 nm, ACN).

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A compound of the formula:

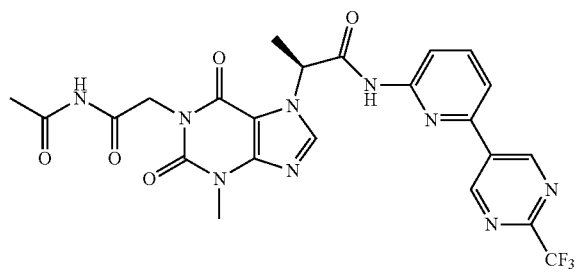 [SMILES: CC(=O)NC(=O)Cn1c(=O)c2c(ncn2[C@@H](C)C(=O)Nc2cccc(-c3cnc(C(F)(F)F)nc3)n2)n(C)c1=O]

wherein the compound is of greater than 95% purity, or a pharmaceutically acceptable salt thereof.

2. A compound of the formula:

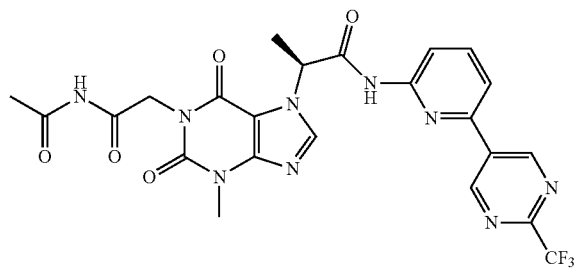 [SMILES: CC(=O)NC(=O)Cn1c(=O)c2c(ncn2[C@@H](C)C(=O)Nc2cccc(-c3cnc(C(F)(F)F)nc3)n2)n(C)c1=O]

wherein the compound is of greater than 95% purity.

3. A pharmaceutical composition, comprising a compound of the formula:

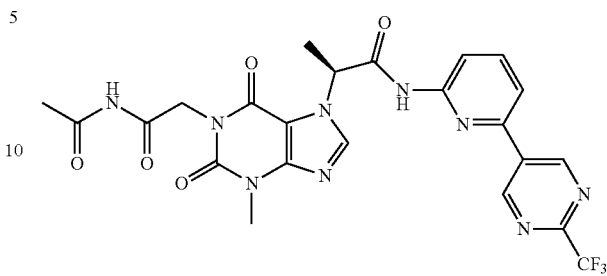

or a pharmaceutically acceptable salt thereof, in a mixture with a pharmaceutically acceptable excipient, diluent, or carrier.

4. A pharmaceutical composition comprising a compound of the formula:

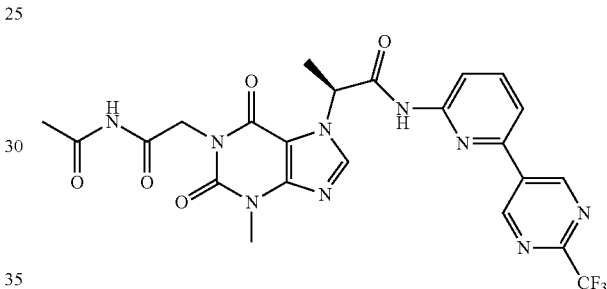

in a mixture with a pharmaceutically acceptable excipient, diluent, or carrier.

5. The pharmaceutical composition according to claim 3 wherein the composition is for oral administration.

6. A method of treating pain in a subject, comprising administering an effective amount of a compound of the formula:

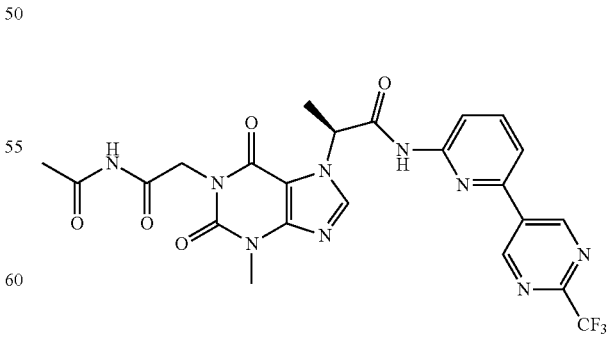

or a pharmaceutically acceptable salt thereof.

7. The method of treating pain in a subject according to claim 6 wherein the compound is:

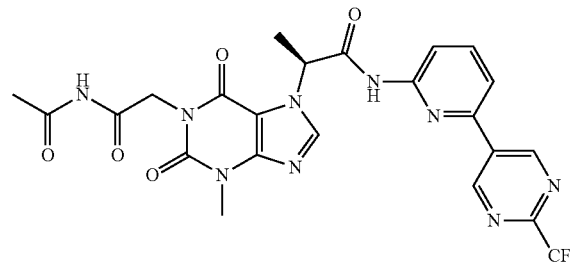

8. A pharmaceutical composition, comprising a compound of the formula:

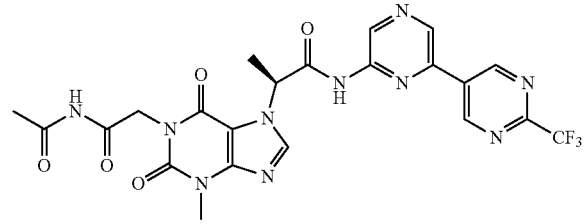 [SMILES: CC(=O)NC(=O)Cn1c(=O)c2c(ncn2[C@@H](C)C(=O)Nc2cncc(-c3cnc(C(F)(F)F)nc3)n2)n(C)c1=O]

or a pharmaceutically acceptable salt thereof, in a mixture with a pharmaceutically acceptable excipient, diluent, or carrier.

9. A method of treating pain in a subject, comprising administering an effective amount of a compound of the formula:

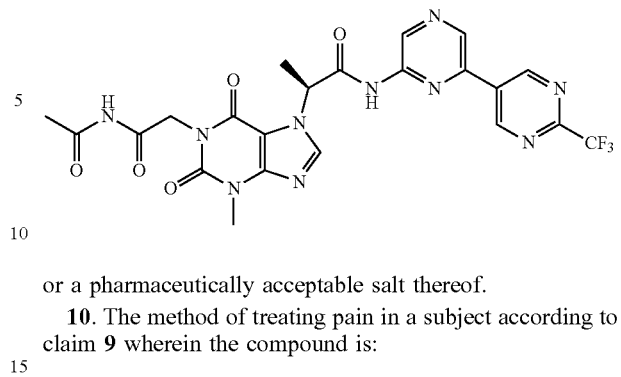

or a pharmaceutically acceptable salt thereof.

10. The method of treating pain in a subject according to claim 9 wherein the compound is:

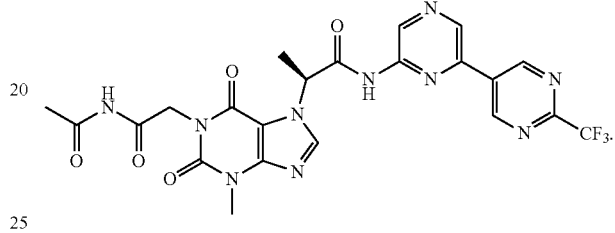

11. The method of claim 6 wherein the pain is chronic pain.

12. The method of claim 7 wherein the pain is chronic pain.

13. The method of claim 9 wherein the pain is chronic pain.

14. The method of claim 10 wherein the pain is chronic pain.

\* \* \* \* \*

UNITED STATES PATENT AND TRADEMARK OFFICE
CERTIFICATE OF CORRECTION

PATENT NO. : 11,161,849 B2  
APPLICATION NO. : 16/763125  
DATED : November 2, 2021  
INVENTOR(S) : Wu Page 1 of 1

It is certified that error appears in the above-identified patent and that said Letters Patent is hereby corrected as shown below:

On the Title Page

Item (54), Line 2, delete "AL" and insert -- A1 --, therefor.

In the Specification

Column 1, Line 2, delete "AL" and insert -- A1 --, therefor.

Signed and Sealed this  
Fifteenth Day of February, 2022

Drew Hirshfeld  
*Performing the Functions and Duties of the*  
*Under Secretary of Commerce for Intellectual Property and*  
*Director of the United States Patent and Trademark Office*